US006664552B2

(12) United States Patent
Shichi et al.

(10) Patent No.: US 6,664,552 B2
(45) Date of Patent: Dec. 16, 2003

(54) METHOD AND APPARATUS FOR SPECIMEN FABRICATION

(75) Inventors: Hiroyasu Shichi, Tokyo (JP); Tohru Ishitani, Hitachinaka (JP); Hidemi Koike, Hitachinaka (JP); Kaoru Umemura, Musashino (JP); Eiichi Seya, Kunitachi (JP); Mitsuo Tokuda, Tachikawa (JP); Satoshi Tomimatsu, Kokubunji (JP); Hideo Kashima, Kokubunji (JP); Muneyuki Fukuda, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 67 days.

(21) Appl. No.: 09/985,537

(22) Filed: Nov. 5, 2001

(65) Prior Publication Data

US 2002/0079463 A1 Jun. 27, 2002

(30) Foreign Application Priority Data

Nov. 6, 2000 (JP) ...................................... 2000-342372
Jul. 5, 2001 (JP) ...................................... 2001-204768

(51) Int. Cl.$^7$ ................................................ G21G 5/00
(52) U.S. Cl. .................................. 250/492.21; 250/307
(58) Field of Search ........................... 250/492.1, 492.2, 250/492.21, 492.3, 492.22, 492.23, 492.24, 309–310

(56) References Cited

U.S. PATENT DOCUMENTS

| | | | | | |
|---|---|---|---|---|---|
| 5,089,774 A | * | 2/1992 | Nakano | ........................ | 324/751 |
| 5,270,552 A | * | 12/1993 | Ohnishi et al. | .............. | 250/307 |
| 5,986,264 A | * | 11/1999 | Grunewald | .................. | 250/310 |
| 6,039,000 A | * | 3/2000 | Libby et al. | .............. | 118/723 E |

FOREIGN PATENT DOCUMENTS

| | | |
|---|---|---|
| JP | 03-166744 | 11/1989 |
| JP | 05-052721 | 8/1991 |
| WO | WO99/05506 | 7/1998 |

OTHER PUBLICATIONS

L.A. Giannuzzi, J.I. Drown, S.R. Brown, R. B. Irwin, F.A. Stevie, "Focused Ion Beam Milling and Micromanipulation Lift–out for Site Specific Cross–Section TEM Specimen Preparation", Material Research Society Symposium Proceeding (1997), vol. 480, pp. 19–27.

L.R. Herlinger, S. Chevacharoenkul, D.C. Erwin, "TEM Sample Preparation Using a Focused Ion Beam and a Probe Manipulator", Proceedings of the 22$^{nd}$ International Symposium for Testing and Failure Analysis, Nov. 18–22, 1996, pp. 199–205.

"Election and Ion Beam Handbook", Third Edition, (Japan Society for the Promotion of Science, 132 commission, Nikkan KKogyo ShinbunSha), pp. 458–461.

* cited by examiner

Primary Examiner—John R. Lee
Assistant Examiner—Christopher M. Kalivoda

(57) ABSTRACT

A sample fabricating method of irradiating a sample with a focused ion beam at an incident angle less than 90 degrees with respect to the surface of the sample, eliminating the peripheral area of a micro sample as a target, turning a specimen stage around a line segment perpendicular to the sample surface as a turn axis, irradiating the sample with the focused ion beam while the incident angle on the sample surface is fixed, and separating the micro sample or preparing the micro sample to be separated. A sample fabricating apparatus for forming a sample section in a sample held on a specimen stage by scanning and deflecting an ion beam, wherein an angle between an optical axis of the ion beam and the surface of the specimen stage is fixed and formation of a sample section is controlled by turning the specimen stage.

2 Claims, 28 Drawing Sheets

ROTATE 180 DEGREE

TILT SPECIMEN STAGE

↓ TILT SPECIMEN STAGE

ROTATE 90 DEGREE

METHOD AND APPARATUS FOR SPECIMEN FABRICATION

BACKGROUND OF THE INVENTION

The present invention relates to method and apparatus specimen fabrication for analyzing, observing, or measuring a micro area by separating a micro sample including a requested specific area from a sample of an electronic part such as a semiconductor wafer or a device or preparing the micro sample to be separated by using a focused ion beam.

Electronic parts such as a semiconductor memory typified by a dynamic random access memory, a microprocessor, a semiconductor device such as a semiconductor laser, and a magnetic head are required to be manufactured in a high yield since decrease in the manufacturing yield due to occurrence of a defect causes profit deterioration. Consequently, early detection/measure of/against a defect, a foreign matter, and poor processing as causes of a failure are big tasks. For example, at a site of manufacturing a semiconductor device, energies are put into finding a failure by a careful test and analyzing the cause of the failure. In an actual electronic part manufacturing process using a wafer, a wafer being processed is tested, the cause of an abnormal portion such as a defect in a circuit pattern or a foreign matter is tracked down, and a measurement to be taken is examined.

Usually, to observe a fine structure of a sample, a scanning electron microscope (hereinbelow, abbreviated as SEM) with high resolution is used. However, as the packing density of a semiconductor device is becoming higher, an object cannot be observed with the resolution of the SEM. Therefore, in place of the SEM, a transmission electron microscope (hereinbelow, abbreviated as TEM) having higher observation resolution is used.

Conventional TEM sample fabrication is accompanied by a work of making a sample into small pieces by cleaving, cutting, or the like. When the sample is a wafer, in most cases, the wafer has to be cut.

Recently, there is a micro area processing method of irradiating a sample with an ion beam and applying an action that particles constructing the sample are released from the sample by sputtering, that is, a method of using a process with a focused ion beam (hereinbelow, abbreviated as FIB). According to the method, first, a strip pellet having a thickness of sub millimeters including an area to be observed is cut from a sample such as a wafer by using a dicer or the like. A part of the strip pellet is processed with an FIB into a thin film state to thereby prepare a TEM sample. The feature of the sample for TEM observation processed with the FIB is that a part of a specimen is processed to a thin film having a thickness of about 100 nm for the TEM observation. Although the method enables a requested observation area to be positioned with accuracy of a micrometer level and to be observed, still, the wafer has to be cut.

Although monitoring a result of a process during fabrication of a semiconductor device or the like has an big advantage from the viewpoint of managing the yield, a wafer is cut for preparation of a sample as described above and a piece of the wafer is not subjected to a following process but is discarded. In recent years, particularly, the diameter of a wafer is increasing to reduce the price of manufacturing a semiconductor device. Specifically, the number of semiconductor devices which can be manufactured from a single wafer is increased to reduce a unit price. However, it increases the price of the wafer itself, an added value increases as the manufacturing process advances and, further, the number of semiconductor devices lost by discarding a wafer increases. Therefore, the conventional test method accompanying cutting of the wafer is very uneconomical.

To deal with the problem, there is a method of preparing a sample without cutting a wafer. The method is disclosed in Japanese Patent Application No. H05-52721, "Method of separating sample and method of analyzing sample separated by the separating method" (known technique 1). According to the method, as shown in FIGS. 2(a) to 2(g), first, the posture of a sample 2 is maintained so that the surface of the sample 2 is irradiated with an FIB 1 at the right angle and scanned with the FIB 1 in a rectangular shape, and a rectangular hole 7 having a required depth is formed in the surface of the sample (FIG. 2(a)) Subsequently, the sample 2 is tilted and a bottom hole 8 is formed. The tilt angle of the sample 2 is changed by a specimen stage (not shown) (FIG. 2(b)). The posture of the sample 2 is changed, the sample 2 is disposed so that the surface of the sample 2 becomes perpendicular to the FIB 1 again, and a trench 9 is formed (FIG. 2(c)). By driving a manipulator (not shown), the tip of a probe 3 at the end of the manipulator is made come into contact with a portion to be separated in the sample 2 (FIG. 2(d)). A deposition gas 5 is supplied from a gas nozzle 10, and an area including the tip of the probe 3 is locally irradiated with the FIB 1 to form an ion beam assist deposition film (hereinbelow, simply called deposition film 4). The separation portion in the sample 2 and the tip of the probe 3 which are in contact with each other are connected to each other by the deposition film 4 (FIG. 2(e)). The peripheral portion is trenched with the FIB 1 (FIG. 2(f)), and a micro sample 6 as a sample separated from the sample 2 is cut. The cut separated sample 6 is supported by the connected probe 3 (FIG. 2(g)). The micro sample 6 is processed with the FIB 1 and the area to be observed is walled, thereby obtaining a TEM sample (not shown). According to the method, a micro sample including a requested analysis area is separated from a sample such as a wafer by using a process with an FIB and means for carrying the micro sample. The micro sample separated by the method is introduced to any of various analyzers and can be analyzed.

A similar sample fabricating method is disclosed in Japanese Patent Application Laid-Open No. H09-196213, "Apparatus and method for preparing micro sample" (known technique 2). According to the method, as shown in FIGS. 9(a) to 9(j), first, the FIB 1 is emitted to form marks 403 and 404 for identifying a target position and, after that, rectangular holes 401 and 402 are formed on both outer sides of the marks 403 and 404 in the sample 2 (FIG. 9(a)). Subsequently, a trench 406 is formed with the FIB 1 (FIG. 9(b)). The specimen stage is tilted and the surface of the sample is obliquely irradiated with the FIB 1, thereby forming a tapered trench 408, and an extraction sample 407 which is connected to the sample 4 only via a residual area 405 is formed (FIG. 9(c)). The tilted specimen stage is returned to the original position and the probe 3 is controlled by a probe controller so as to come into contact with a part of the extraction sample 407. The residual area 405 of the extraction sample 407 will be cut with an FIB later. In consideration of a probe drift or the like, it is desirable to cut the residual area 405 in short time, so that the volume of the residual area 405 has to be low. Consequently, due to a fear that the residual area 405 is destroyed by the contact of the probe 3, the probe 3 is made contact while preventing a damage as much as possible by using the probe controlling method. The probe 3 and the extraction sample 407 which are in contact with each other are fixed by using a deposition film 409 (FIG. 9(d)) Subsequently, the residual area 405 is cut with the FIB 1 (FIG. 9(e)). In such a manner, the extraction sample 407 is cut out, and the probe 3 is lifted by the probe driving apparatus to extract the extraction sample 407 (FIG. 9(f)). Subsequently, the cut extraction sample 407 is allowed to come into contact with a trench 411 formed in an extracted sample holder (FIG. 9(g)). At this time, the extraction sample 407 has to come into contact at a sufficiently low speed so that the extraction sample 407 is not destroyed or is not come off from the connected portion with the deposition film 409, so that the contacting method is necessary. After making the extraction sample 407 contact with the trench 411, they are fixed by using a deposition film 412 (FIG. 9(h)). After the fixing, the probe 3 connection portion is irradiated with the FIB, and sputtering is performed to separate the probe from the extraction sample 407 (FIG. 9(i)) In the case of preparing a TEM sample, finally, the FIB 1 is emitted again to finish an observation area 410 so that the thickness of the observation area 410 becomes about 100 nm or less (FIG. 9(j)). In the case of preparing a sample for analysis or measurement, the finishing process for making the observation area thin (FIG. 9(j)) is not always necessary.

The example of employing the method of extracting a micro sample by the sample fabricating apparatus has been described above. There is also a method of processing the shape of a micro sample by the sample fabricating apparatus, taking out the base from the sample fabricating apparatus, and extracting the micro sample by another mechanism in atmosphere. For example, such a method is described by L. A. Giannuzzi et al., "Focused Ion Beam Milling and Micromanipulation Lift-Out for Site Specific Cross-Section TEM Specimen Preparation", Material Research Society, Symposium Proceeding Vol. 480, pp. 19 to 27 (known technique 3). Similarly, it is also described by L. R. Herlinger, "TEM Sample Preparation Using a Focused Ion Beam and a Probe Manipulator", Proceedings of the 22nd International Symposium for Testing and Failure Analysis, pp. 199 to 205 (known technique 4).

According to such a method, as shown in FIG. 3(a), both sides of a target position on a wafer 208 are processed in a stair shape with the FIB 1 to form a sample membrane 207, a specimen stage is tilted to change the angle formed between the FIB 1 and the surface of the sample, and the sample is irradiated with the FIB 1. As shown in FIG. 3(b), the periphery of the sample membrane 207 is cut with the FIB 1, thereby separating the sample membrane 207 from the wafer. The wafer is taken out from an FIB system, a glass stick is allowed to approach the process portion in the atmosphere, the sample membrane 207 is attracted by the glass stick by using static electricity and is separated from the wafer, the glass stick is moved above a mesh 209 and is attracted by the mesh 209 by using static electricity or disposed so that the process face faces a transparent attachment. As described above, the processed micro sample in the system may not be taken out in the system. Even when most of the outer shape of the micro sample is processed with an ion beam, the separated micro sample is introduced into the TEM, and can be analyzed.

By using any of the methods, without cutting a wafer, only a micro sample or a membrane sample for test is extracted from a sample, and the wafer from which the sample is extracted can be returned to the next process. Therefore, unlike the conventional techniques, there is no semiconductor device which is lost by the cutting of a wafer, the manufacturing yield of the semiconductor device is increased in total, and the manufacturing cost can be reduced.

In the case of forming a hole by using sputtering of irradiating the surface of a sample with an ion beam and observing a section of the hole by an FIB system or a scanning electron microscope (SEM), the section is formed at an end of an ion beam scan range.

However, the actually formed section is not perfectly perpendicular to the surface of a sample due to flare of a processing beam and re-deposition of a sputtered substance, and a slight taper exists. An FIB system having a mechanism of tilting a specimen stage can prevent the taper by tilting a sample by an angle corresponding to the taper, for example, about 0.5 degree and irradiating the tilted sample with an ion beam and form an observation section having higher perpendicularity. The method is described as, for example, processing of a sample section of a transmission electron microscope (TEM), in "Electron and ion beam handbook, Third Edition", Japan Society for the Promotion of Science, 132 commission, Nikkan Kogyo Shinbun Sha, pp. 459 and 460 (known technique 5).

The conventional methods have the following problems. Specifically, to form the bottom hole 8 in the first known technique, to form the tapered trench 408 in the second known technique, and to cut the periphery of the sample membrane 207 in the fourth known technique, the posture or tilt angle of the sample 2 is changed as a necessary process by the specimen stage. However, as the diameter of a wafer increases, the specimen stage also becomes larger. Consequently, a problem such that it takes time to tile a large stage with high accuracy and, as a result, sample fabrication time becomes longer arises. Due to heavy weight of the specimen stage itself, the eucentric is not maintained before and after the tilting and the sample position relative to the ion beam irradiating optical system moves, so that the focal point of the FIB is relatively largely deviated from the surface of the sample, the surface of the sample cannot be observed, and a problem such that the ion beam irradiating optical system has to be re-adjusted also occurs. The function of tilting the specimen stage causes increase in the size of the specimen stage itself and in the size of a specimen chamber for housing the specimen stage. The trend of the diameter of a wafer is shifting from 200 mm to 300 mm. When the diameter of a wafer is further increased to 400 mm, the size of the stage has to be increased and the problem which occurs in association with the tilt of the specimen stage has to be solved. In contrast, when the function of tilting the specimen stage of the system can be eliminated, miniaturization of the whole system can be realized and a problem such as a deviation of the sample position accompanying a tilt of the sample is solved. However, by the above-described conventional methods, fabrication of a sample for analyzing, observing or measuring a micro area by separating a micro sample from an original sample (wafer) or preparing the micro sample to be separated cannot be realized. Originally, the change in the tilt angle or posture of a sample is required due to existence of the fixed idea that the surface of a sample has to be irradiated with ion beams in at least two directions at different angles to separate a micro sample from an original sample or prepare the micro sample to be separated. The tilting of the stage denotes here turning of a stage around a line segment included in or parallel to the stage plane as an axis. It will be simply described as tilting of a stage herein later.

By an FIB controller in which a specimen stage has the tilting function, an FIB can be emitted at an arbitrary angle, and can eliminate the taper as in the known technique 5.

On the other hand, the function of tilting a specimen stage can be omitted from the system, the miniaturization of the whole system is realized, and the program such as a deviation of the sample position which occurs in association with the tilting of a sample can be solved. However, according to the conventional methods, it is difficult to emit an FIB at an arbitrary angle. A method of obliquely irradiating the surface of a sample with an ion beam to form a hole, there by enabling an observation section to be formed is disclosed as "Section observing method" in Japanese Patent Application Laid-Open No. H03-166744 (known technique 6). Although a process of forming a vertical section by the method is described, a method of optionally changing an irradiation angle without tilting a specimen stage is not mentioned. Consequently, it is difficult to eliminate the taper.

SUMMARY OF THE INVENTION

In consideration of the problems, a first object of the invention is to provide a sample fabricating method for analyzing, observing, or measuring a micro area by separating a micro sample including a requested specific area from an original sample of an electronic part such as a semiconductor wafer, a semiconductor device, or the like or preparing the micro sample to be separated without tilting a specimen stage by breaking down the conventional fixed idea. A second object is to provide a sample fabricating apparatus suitable for achieving the first object. A third object is to realize a sample fabricating apparatus and a sample fabricating method which can form a section by irradiation with an FIB at an arbitrary angle in a certain range even when a not-tilting specimen stage is used.

Terms used in the specification will be defined as follows.

A requested section is a section the operator of the apparatus intends to prepare. A set section denotes a section obtained when it is assumed that a set ion beam scanning area is ideally processed without an influence of a beam diameter, re-deposition, or the like. A formed section is a section actually formed with an FIB. A formed-section edge is a cross line between the formed section and the surface of a sample. A set-section edge is a cross line between the set section and the surface of a sample. A scanning-area edge is one of the sides of an ion bean scanning area. A requested-section edge is a cross line of a requested section and the surface of a sample. A requested-section edge normal direction is a direction of a normal line in a sample surface of a requested section edge, which extends from the sample to a process space. A requested section normal direction is a direction of a normal line of a requested section, which extends from the inside of the sample to a process space. A requested depression angle is an angle formed between the requested-section normal direction and the sample surface. The requested depression angle is positive in the case where the requested-section normal line direction extends from the sample surface to the inside of the sample, and is negative in the case where the requested-section normal line direction extends from the inside of the sample to the surface of the sample (corresponding to an elevation angle). A set-section depression angle is an angle formed between the set-section normal line direction and the sample surface. The set-section depression angle is positive when the set-section normal line direction extends from the sample surface to the inside of the sample and is negative when the set-section normal line direction extends from the inside of the sample to the surface of the sample (corresponding to an elevation angle).

The first object of the invention is achieved as follows.

Basic aspects of the invention to break down the conventional fixed idea that the tilt angle or the posture of a sample has to be changed are as follows.

(1) An ion beam processing method for separating a requested portion in a sample or preparing the requested portion by irradiating the sample with an ion beam from a plurality of directions while fixing an angle formed between a sample placement face and an optical axis of an ion beam to the sample.

According to the invention, the ion beam processing method for analyzing, observing, or measuring a micro area by separating a micro sample including a requested specific area from a sample of an electronic part such as a semiconductor wafer, a semiconductor device, or the like or preparing the micro sample without tilting a specimen stage can be realized.

(2) A sample separating method for irradiating a sample with an ion beam while setting an angle formed between the optical axis of the ion beam emitted to the sample and the surface of the sample to be larger than 0 degree and smaller than 90 degrees and irradiating a requested portion in the sample with the ion beam while fixing an angle formed between the optical axis of the ion beam emitted to the sample and the sample surface to thereby separate the requested portion or prepare the requested portion to be separated.

According to the invention, the sample fabricating method for analyzing, observing, or measuring a micro area by separating a micro sample including a requested specific area from a sample of an electronic part such as a semiconductor wafer, a semiconductor device, or the like or preparing the micro sample without tilting a specimen stage can be realized.

(3) A sample separating method for irradiating a sample with an ion beam while setting an angle formed between the optical axis of the ion beam emitted to the sample and the sample surface to be a range from 30 degrees to 75 degrees, and irradiating a requested portion in the sample with the ion beam while fixing the angle formed between the optical axis of the ion beam emitted to the sample and the sample surface, thereby separating the requested portion or preparing the requested portion to be separated.

According to the invention, the sample fabricating method for analyzing, observing, or measuring a micro area by separating a micro sample including a requested specific area from a sample of an electronic part such as a semiconductor wafer, a semiconductor device, or the like or preparing the micro sample without tilting a specimen stage can be realized. Particularly, by setting the FIB irradiation angle in the range from 30 degrees to 75 degrees, the surface of the sample can be observed excellently, and the shape of the micro sample is formed to be suitable for fabrication.

(4) The object is also realized by a sample fabricating method for separating a micro sample from a sample or preparing the micro sample to be separated by using a sample fabricating apparatus including at least a focused ion beam irradiating optical system, secondary particle detecting means for detecting secondary particles generated from a sample irradiated with the focused ion beam, and a specimen stage on which a specimen base is placed, in which the sample is irradiated with the focused ion beam by setting the angle formed between the optical axis of the focused ion beam emitted to the sample and the sample surface to be larger than 0 degree and smaller than 90 degrees, and the sample is turned by using a sample surface normal line as a turning axis and is irradiated with the ion beam while fixing the angle formed between the optical axis of the focused ion beam to the sample and the sample surface.

That is, an aspect of the invention for breaking down the conventional fixed idea is to include an operation of turning a specimen stage around the line normal to the sample surface as a turning axis into the sample fabricating method in accordance with an object. According to the invention, the sample fabricating method for analyzing, observing, or measuring a micro area by separating a micro sample including a requested specific area from a sample of an electronic part such as a semiconductor wafer, a semiconductor device, or the like or preparing the micro sample without tilting a specimen stage can be realized.

Also in the case of an apparatus in which the specimen stage has the tilting function, the time required to tilt the stage is unnecessary so that the sample fabricating time is made relatively short. The problem such that the sample surface cannot be observed before and after the specimen stage is tilted is also reduced.

(5) In the sample fabrication method of (4), the requested portion in the sample is supported by a probe.

According to the invention, the sample fabricating method for analyzing, observing, or measuring a micro area by separating a micro sample including a requested specific area from a sample of an electronic part such as a semiconductor wafer, a semiconductor device, or the like or preparing the micro sample without tilting a specimen stage can be realized. By supporting the micro sample by the probe and extracting the micro sample from the specimen base, the section of the micro sample can be observed in detail, and the position of processing the section can be controlled with high precision. As the method of supporting the micro sample, any method can be used as long as the micro sample can be supported such as fixing by using a deposition film, fixing by using static electricity, or the like.

(6) A sample fabricating method for observation, analysis, or measurement, including: a step of forming a sample connected to a specimen base via a residual area by a step of forming a rectangle hole by irradiating the sample with a focused ion beam while setting an angle formed between the optical axis of the focused ion beam emitted to the sample and the sample surface to be larger than 0 degree and smaller than 90 degrees, a step of turning the sample by using a sample surface normal line as a turning axis, and a step of forming a tapered trench in the surface of the specimen base by emitting a focused ion beam after the turn; a step of fixing the connected sample to a requested portion of transfer means by making a requested portion in the connected sample contact with the requested portion of the transfer means, and forming a deposition film in an area including the contact portion by irradiating the area with a focused ion beam while supplying a deposition gas; and a step of cutting the residual area by emitting a focused ion beam.

According to the invention, the sample fabricating method for analyzing, observing, or measuring a micro area by separating a micro sample including a requested specific area from a sample of an electronic part such as a semiconductor wafer, a semiconductor device, or the like or preparing the micro sample without tilting a specimen stage can be realized. The section of the micro sample can be observed in detail, and the section process position can be controlled with high precision.

(7) A sample fabricating method for observation, analysis, or measurement, including: a step of forming a membrane by forming a rectangle hole by emitting a focused ion beam while setting an angle formed between the optical axis of the focused ion beam emitted to the sample and the sample surface to be larger than 0 degree and smaller than 90 degrees; a step of turning the sample by using a sample surface normal line as a turning axis, and a step of separating the sample membrane or preparing the sample membrane to be separated by emitting a focused ion beam after the turn.

According to the invention, the sample fabricating method for analyzing, observing, or measuring a micro area by separating a micro sample including a requested specific area from a sample of an electronic part such as a semiconductor wafer, a semiconductor device, or the like or preparing the micro sample without tilting a specimen stage can be realized. Since a process of forming an ion beam assist deposition film or the like is not included, the sample fabrication time can be shortened.

(8) In the sample fabricating method in any of (3), (4), (5), (6), and (7), in order to separate at least two micro samples or prepare the micro samples to be separated, the peripheral area of each of micro samples is processed to some midpoint of all the processes, the sample is turned, and the process of the peripheral area of each of the micro samples is sequentially continued.

According to the invention, the sample fabricating method for analyzing, observing, or measuring a micro area by separating a micro sample including a requested specific area from a sample of an electronic part such as a semiconductor wafer, a semiconductor device, or the like or preparing the micro sample without tilting a specimen stage can be realized. Particularly, a plurality of samples can be prepared with high throughput.

The second object of the invention is achieved as follows.

(9) A sample fabricating apparatus including at least a focused ion beam irradiating optical system and a specimen stage on which a specimen base is placed, for separating a micro sample from the specimen base or preparing the micro sample to be separated, wherein an angle formed between an almost center axis of a mechanical column including the focused ion beam irradiating optical system and the sample placement face of the specimen stage is fixed, and the apparatus has a separator for separating a desired portion in the sample and a probe for supporting the separated sample.

According to the invention, the sample fabricating method for analyzing, observing, or measuring a micro area by separating a micro sample including a requested specific area from a sample of an electronic part such as a semiconductor wafer, a semiconductor device, or the like or preparing the micro sample without tilting a specimen stage can be realized. By supporting the micro sample by the probe and extracting the micro sample from the specimen base, the section of the micro sample can be observed in detail, and the sample fabricating apparatus capable of controlling the section process position with high precision can be realized. As the method of supporting the micro sample, any method can be used as long as the micro sample can be supported such as fixing by using a deposition film, fixing by using static electricity, or the like.

(10) A sample fabricating apparatus for separating a micro sample from a specimen base or preparing the micro sample to be separated, including at least a focused ion beam irradiating optical system, secondary particle detecting means for detecting secondary particles generated from a sample irradiated with the focused ion beam, and a specimen stage on which a specimen base is placed, wherein the angle formed between the optical axis of the focused ion beam emitted to the sample and the sample surface is larger than 0 degree and smaller than 90 degrees, the specimen stage has the function of turning around a sample surface normal line as a turn axis, and the apparatus has the function of determining, after the turn, the position irradiated with the focused ion beam for separating a sample or preparing the sample to be separated by using image displaying means for displaying a secondary particle image formed by secondary particles generated from the sample irradiated with the focused ion beam or an electron beam emitted from an electron beam emitting system separately provided.

According to the invention, the sample fabricating apparatus for preparing a sample for analyzing, observing, or measuring a micro area by separating a micro sample including a requested specific area from a sample of an electronic part such as a semiconductor wafer, a semiconductor device, or the like or preparing the micro sample to be separated without tilting the specimen stage, which is suitable from the viewpoints that operations of the apparatus can be automated and the burden on the operator can be lessened and can prepare a sample in which a damage in the sample surface is little in a short time can be realized.

(11) A sample fabricating apparatus for separating a micro sample from a specimen base or preparing the micro sample to be separated, including at least a focused ion beam irradiating optical system, secondary particle detecting means for detecting secondary particles generated from a sample irradiated with the focused ion beam, and a specimen stage on which a specimen base is placed, wherein the angle formed between the optical axis of the focused ion beam emitted to the sample and the sample surface is larger than 0 degree and smaller than 90 degrees, the specimen stage has the function of turning around a sample surface normal line as a turn axis, and the apparatus has the function of determining, after the turn, the position irradiated with the focused ion beam for separating a sample or preparing the sample to be separated by using a result of performing an image process on a secondary particle image formed by secondary particles generated from the sample irradiated with the focused ion beam or an electron beam emitted from an electron beam emitting system separately provided.

According to the invention, the sample fabricating apparatus for preparing a sample for analyzing, observing, or measuring a micro area by separating a micro sample including a requested specific area from a sample of an electronic part such as a semiconductor wafer, a semiconductor device, or the like or preparing the micro sample to be separated without tilting the specimen stage, which is suitable from the viewpoints that operations of the apparatus can be automated and the burden on the operator can be lessened and can prepare a sample in which a damage in the sample surface is little in a short time can be realized.

(12) A sample fabricating apparatus for separating a micro sample from a specimen base or preparing the micro sample to be separated, including at least a focused ion beam irradiating optical system, secondary particle detecting means for detecting secondary particles generated from a sample irradiated with the focused ion beam, and a specimen stage on which a specimen base is placed, wherein the angle formed between the focused ion beam irradiating optical system and the sample surface is in a range from 30 degrees to 75 degrees, the specimen stage has a turning function around a normal line to the sample surface as a rotation axis, and the apparatus includes a transfer means for transferring an extracted micro sample which is a desired portion separated from the specimen base to another member, and a holding means of a sample holder on which the extracted micro sample is placed.

The sample fabricating apparatus is suitable for fabricating a sample for analyzing, observing, and measuring a micro area by separating a micro sample including a requested specific area from a sample of an electronic part such as a semiconductor wafer, a semiconductor device, or the like or preparing the micro sample to be separated without tilting the specimen stage. Particularly, by irradiating the focused ion beam at an angle from 30 degrees to 75 degrees, the surface of the sample can be observed excellently, and the shape of the micro sample is suitable for easy fabrication. The sample fabricating apparatus capable of fabricating a sample in shorter time can be realized.

(13) A sample fabricating apparatus for separating a micro sample from a specimen base or preparing the micro sample to be separated, including at least a focused ion beam irradiating optical system, secondary particle detecting means for detecting secondary particles generated from a sample irradiated with the focused ion beam, and a specimen stage on which a specimen base is placed, in which the angle formed between the optical axis of the focused ion beam emitted to the sample and the sample surface is 45 degrees, the specimen stage has a function of turning around a sample surface normal line as a rotation axis, and the apparatus includes a transfer means for transferring an extracted micro sample which is a requested portion separated from the specimen base to another member, and a holding means of a sample holder on which the extracted micro sample is placed.

According to the invention, the sample fabricating apparatus for preparing a sample for analyzing, observing, or measuring a micro area by separating a micro sample including a requested specific area from a sample of an electronic part such as a semiconductor wafer, a semiconductor device, or the like or by preparing the micro sample to be separated without tilting the specimen stage can be realized. The apparatus is suitable for separating a sample or preparing the sample to be separated since the angle of the focused ion beam can be set to 45 degrees in both of the cases of observing the sample surface and a section of the sample by irradiation with the focused ion beam under the same conditions. Further, the sample fabricating apparatus capable of preparing a sample having little damage in its surface in a short time can be realized.

(14) In the sample fabricating apparatus in any of (10), (11) (12), and (13), the optical axis of the focused ion beam emitted to the sample almost coincides with the mechanical center axis of an objective lens almost symmetrical with respect to the center as a component of the focused ion beam irradiating optical system.

According to the invention, the sample fabricating apparatus capable of fabricating a sample for analyzing, observing, or measuring a micro area by separating a micro sample including a requested specific area from a sample of an electronic part such as a semiconductor wafer, a semiconductor device, or the like or preparing the micro sample to be separated without tilting the specimen stage can be realized by mechanically specifying the angle formed between the objective lens almost symmetrical with respect to the center as a component of the focused ion beam irradiating optical system and the surface of the specimen stage, so that designing of the apparatus can be simplified.

(15) As ample fabricating apparatus including at least a focused ion beam irradiating optical system, secondary particle detecting means for detecting secondary particles generated from a sample irradiated with the focused ion beam, and a specimen stage on which a specimen base is placed, in order to separate a micro sample from the specimen base or preparing the micro sample to be separated, for irradiating a peripheral area of the micro sample in the specimen stage with the focused ion beam from a plurality of incident directions to thereby separate the micro sample or prepare the micro sample to be separated, in which the focused ion beam irradiating optical system is provided with a focused ion beam tilting function of changing the optical axis of the focused ion beam emitted to the sample by at least 15 degrees.

According to the invention, the sample fabricating apparatus capable of fabricating a sample for analyzing, observing, or measuring a micro area by separating a micro sample including a requested specific area from a sample of an electronic part such as a semiconductor wafer, a semiconductor device, or the like or preparing the micro sample to be separated without tilting the specimen stage can be realized by the focused ion beam tilting function capable of changing the incident direction of the focused ion beam at least by 15 degrees. Particularly, the focused ion beam incident angle can be selected in preparation of a sample, so that various sample fabricating methods and various sample shapes can be realized.

(16) In the sample fabricating apparatus of (15), the focused ion beam tilting function capable of changing the optical axis of the focused ion beam emitted to the sample by at least 15 degrees is realized by a mechanism of varying the tilt angle with respect to the specimen stage of a mechanical column including the focused ion beam irradiating optical system.

According to the invention, the sample fabricating apparatus capable of fabricating a sample for analyzing, observing, or measuring a micro area by separating a micro sample including a requested specific area from a sample of an electronic part such as a semiconductor wafer, a semiconductor device, or the like or preparing the micro sample to be separated without tilting the specimen stage can be realized by the mechanism of varying the tilt angle with respect to the specimen stage of the mechanical column including the focused ion beam irradiating optical system. Particularly, the focused ion beam incident angle can be selected in preparation of a sample, so that various sample fabricating methods and various sample shapes can be realized.

(17) In the sample fabricating apparatus of (15), the focused ion beam tilting function capable of changing the optical axis of the focused ion beam emitted tot he sample by at least 15 degrees is realized by an electric deflecting mechanism.

According to the invention, the sample fabricating apparatus capable of fabricating a sample for analyzing, observing, or measuring a micro area by separating a micro sample including a requested specific area from a sample of an electronic part such as a semiconductor wafer, a semiconductor device, or the like or preparing the micro sample to be separated without tilting the specimen stage can be realized by the electric deflecting mechanism. Particularly, the mechanical apparatus configuration is simplified, the manufacturing cost can be reduced, and the focused ion beam incident angle can be selected in preparation of a sample, so that various sample fabricating methods and various sample shapes can be realized.

(18) In the sample fabricating apparatus in any of (10), (11) (12), (13), (14), (15), (16), and (17), the specimen stage has a fixed tilt angle using a line segment included in the stage plane or a line segment parallel to the stage plane as a tilt axis.

According to the invention, since the specimen stage does not have the tilting function, miniaturization of the whole apparatus can be realized, and the sample fabricating apparatus capable of fabricating a sample for analyzing, observing, and measuring a micro area by separating a micro sample including a requested specific area from a sample of an electronic part such as a semiconductor wafer, a semiconductor device, or the like or preparing the micro sample to be separated can be realized.

(19) In the sample fabricating apparatus in any of (9), (10), (11), (12), (13), (14), (15), (16), and (17), the specimen stage is constructed by combining a stage which is turned at a specific fixed angle and a stage which can be turned at an arbitrary angle.

According to the invention, since the specimen stage does not have the tilting function, miniaturization of the whole apparatus can be realized, and the sample fabricating apparatus capable of fabricating a sample for analyzing, observing, and measuring a micro area by separating a micro sample including a requested specific area from a sample of an electronic part such as a semiconductor wafer, a semiconductor device, or the like or preparing the micro sample to be separated can be realized. Particularly, the apparatus is suitable for saving the time necessary for positioning and increasing the through put of sample preparation.

(20) In the sample fabricating apparatus in any of (9), (10) (11), (12), (13), (14), (15) (16), and (17), the specimen stage is constructed by combining a stage which is turned at a fixed angle that is at least one of 90 degrees and 180 degrees and a stage which can be turned at an arbitrary angle.

According to the invention, since the specimen stage does not have the tilting function, miniaturization of the whole apparatus can be realized, and the sample fabricating apparatus capable of fabricating a sample for analyzing, observing, and measuring a micro area by separating a micro sample including a requested specific area from a sample of an electronic part such as a semiconductor wafer, a semiconductor device, or the like or preparing the micro sample to be separated can be realized. Particularly, the apparatus is suitable for saving the time necessary for positioning and increasing the through put of sample preparation.

The third object of the invention is achieved by the following.

(21) As ample fabricating apparatus for forming a sample section in a sample by ion beam processing, including anion beam optical system constructed by an ion source, a lens for condensing ions emitted from the ion source, and a deflector, anion beam optical system controller for controlling the ion beam optical system, a detector for detecting secondary particles generated from a sample irradiated with an ion beam, a specimen stage for holding the sample, and a specimen-stage position controller for controlling the position of the specimen stage, in which an angle formed between the optical axis of the ion beam emitted from the ion beam optical system and the sample surface is fixed and formation of a sample section is controlled in correspondence with a set-section depression angle. Thus, also in the apparatus in which the tilting of the specimen stage with respect to the ion beam optical system cannot be changed, a section at an arbitrary tilt angle can be formed.

(22) As ample fabricating apparatus for forming a sample section in a sample by ion beam processing, including an ion beam optical system constructed by an ion source, a lens for condensing ions emitted from the ion source, and a deflector, an ion beam optical system controller for controlling the ion beam optical system, a detector for detecting secondary particles generated from a sample irradiated with an ion beam, a specimen stage for holding the sample, and a specimen-stage position controller for controlling the position of the specimen stage, in which the ion beam optical system controller has a construction that an angle formed between the optical axis of the ion beam emitted from the ion beam optical system and the sample surface is larger than 0 degree and smaller than 90 degrees, and controls an ion beam scan by the deflector in correspondence with a set-section depression angle of a set section. Thus, the FIB irradiating angle at the time of processing a section can be arbitrarily set.

(23) In the sample fabricating apparatus in each of (21) and (22), the ion beam optical system controller controls the deflector on the basis of angle information that a requested depression angle is projected to a plane including, as a normal line, the optical axis of the ion beam in correspondence with a set-section depression angle of a set section. Thus, the ion beam processing set angle is controlled and the FIB irradiating angle at the time of processing a section can be arbitrarily set.

(24) In the sample fabricating apparatus in each of (21) and (22), the ion beam optical system controller controls the deflector on the basis of angle information that a set-section depression angle is projected to a plane including, as a normal line, the optical axis of the ion beam in correspondence with a set-section depression angle of a set section, and the specimen-stage position controller controls turning in the specimen stage plane of the specimen stage. Thus, a section at an arbitrary depression angle can be easily formed in an arbitrary processing position by turning a sample.

(25) In the sample fabricating apparatus in any of (21) to (24) angle information that a set-section depression angle of a set section is projected to a plane including, as a normal line, the optical axis of the ion beam is displayed on a display for displaying secondary particle information detected by the secondary particle detector and is set. With the configuration, the operator can visually make processing setting corresponding to a requested FIB irradiating angle.

(26) In the sample fabricating apparatus in each of (21) and (22), in correspondence with parameters of coordinates of a requested-section edge, a requested-section normal line direction, and a size, parameters equivalent to the parameters, or a combination of those parameters, the ion beam optical system controller controls the ion beam deflector, and the specimen-stage position controller controls turn in the specimen stage plane of the specimen stage. With the configuration, processing setting corresponding to section forming parameters desired by the operator can be automated.

(27) In the sample fabricating apparatus in any of (21) to (26), an input apparatus for setting a requested-section depression angle of a requested section or a parameter equivalent to the requested-section depression angle is provided. With the configuration, the operator can easily set the depression angle of the requested section.

(28) A sample fabricating method for irradiating a sample with an ion beam from an oblique direction to prepare a section by sputtering, including a step of setting a depression angle of a section requested to be observed in a sample, a step of determining a scanning-area edge of an ion beam in corresponding to the depression angle and setting a scanning area, and a step of processing the scanning area with the ion beam. Only by deflecting the ion beam, a section at an arbitrary tilt angle in a certain range can be formed.

(29) In the sample fabricating method of (28), by preparing a sample from a step of obtaining a turn angle of the requested section and a step of determining a turn angle of the sample in correspondence with the depression angle and the turn angle of the requested section, and setting turn in the specimen stage plane of the specimen stage, a section at an arbitrary tilt angle in a certain range in the requested section position can be formed.

(30) In a sample fabricating apparatus for forming a sample section in a sample held on a specimen stage by processing with a charged particle beam by using a charged particle beam optical system for condensing, scanning and deflecting a charged particle beam emitted from a charged particle source, an angle formed between the optical axis of the charged particle beam emitted from the charged particle beam optical system and a surface of the specimen stage is fixed, and formation of a sample section is controlled by turning of the specimen stage in the specimen stage plane.

(31) In a sample fabricating apparatus for forming a sample section in a sample held on a specimen stage by processing with a charged particle beam by using a charged particle beam optical system for condensing, scanning and deflecting a charged particle beam emitted from a charged particle source, an angle formed between the optical axis of the charged particle beam emitted from the charged particle beam optical system and a surface of the sample is fixed, and the scanning and deflection of the charged particle beam optical system is controlled in correspondence with an angle formed between a direction of a normal line of a section which is set for forming a sample section requested to be observed in the sample and the surface of the sample.

DETAILED DESCRIPTION OF THE PREFERRED EMBODIMENTS

An embodiment of a sample fabricating apparatus according to the invention includes at least: a focused ion beam irradiating optical system disposed so that a focused ion beam is emitted at an angle formed between the surface of a sample on a stage and the optical axis of a focused ion beam, larger than 0 degree and smaller than 90 degrees; secondary electron detecting means for detecting secondary electrons generated from the sample irradiated with the focused ion beam; and a specimen stage of a structure having no tilting mechanism.

Concrete embodiments will be described hereinbelow.

First Embodiment

Figure 1A:
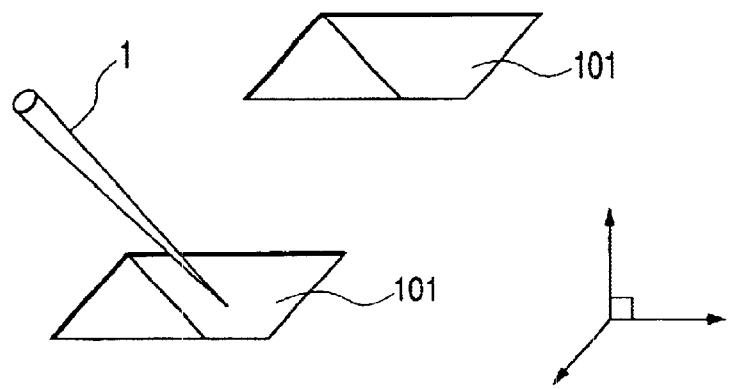
FIGS. 1(a) to 1(f) are diagrams for explaining an embodiment of a sample fabrication method according to the invention.
Figure 1B:
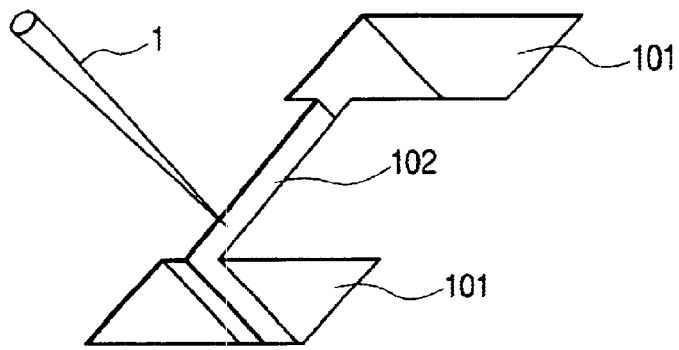
Figure 1B:
Figure 1C:
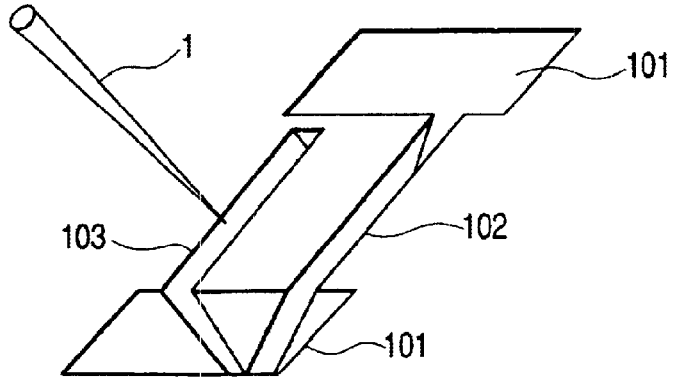
Figure 1D:
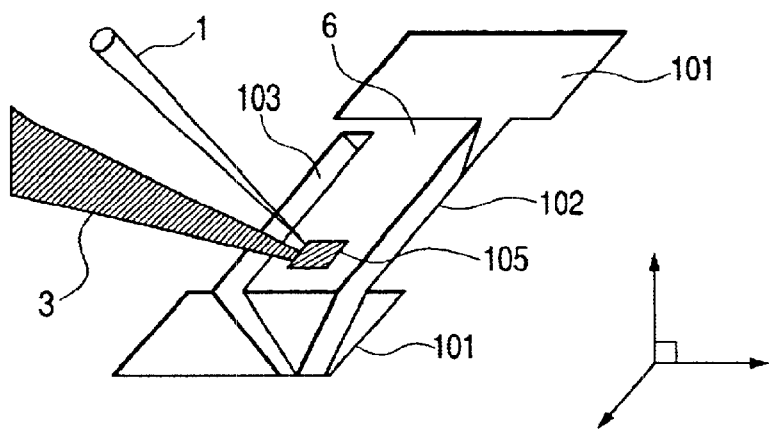
Figure 1E:
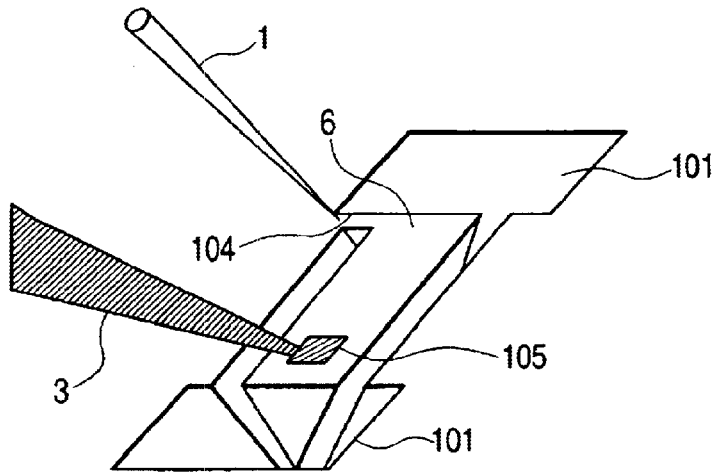
Figure 1F:
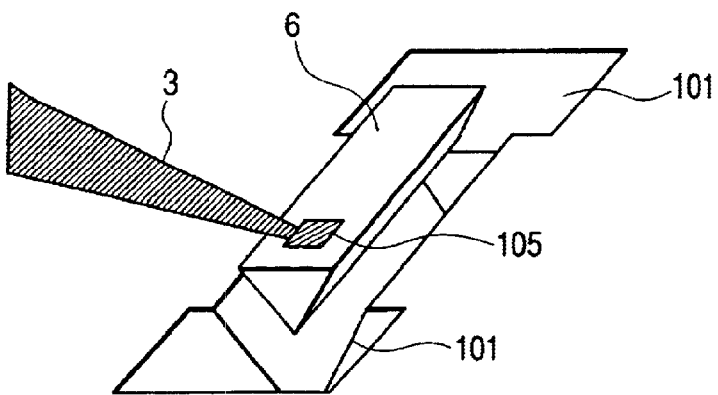
Figure 2A:
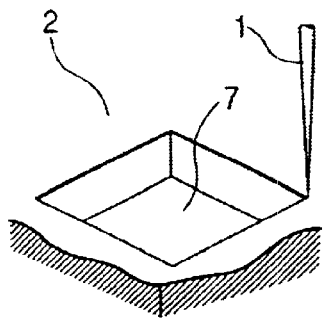
FIGS. 2(a) to 2(g) are diagrams for explaining a conventional method of preparing a TEM sample and, particularly, an example of using an FIB and carrying means.
Figure 2B:
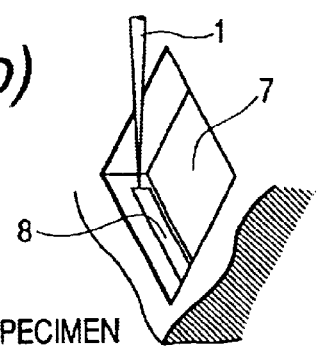
Figure 2C:
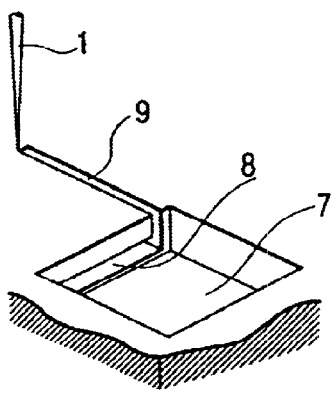
Figure 2D:
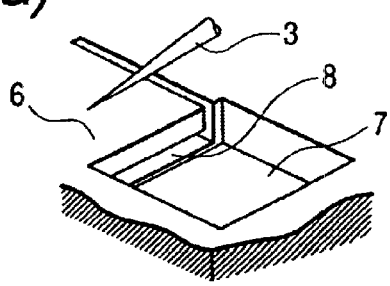
Figure 2E:
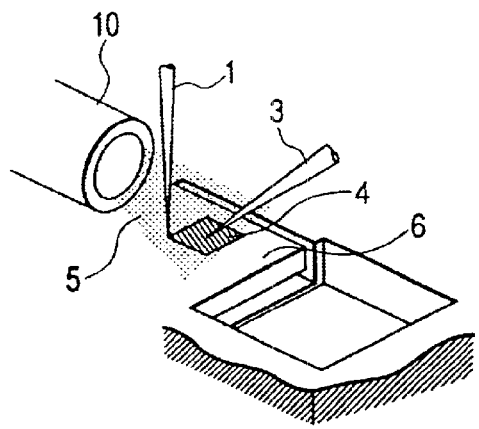
Figure 2F:
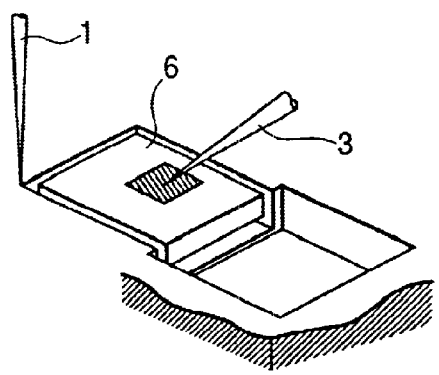
Figure 2G:
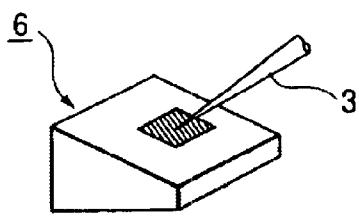
Figure 3A:
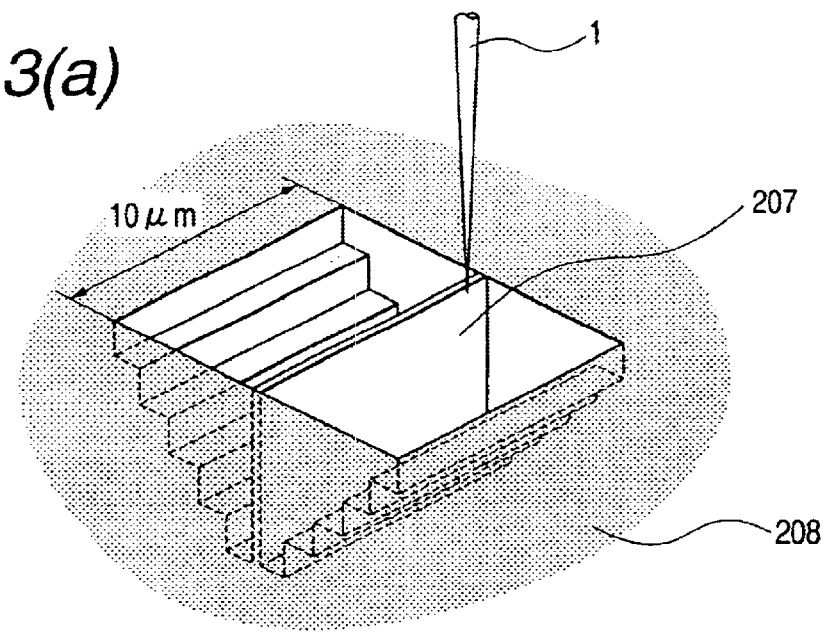
FIGS. 3(a) and 3(b) are diagrams for explaining the conventional method of preparing a TEM sample and, particularly, an example of separating a thin film from a specimen base with an FIB.
Figure 3B:
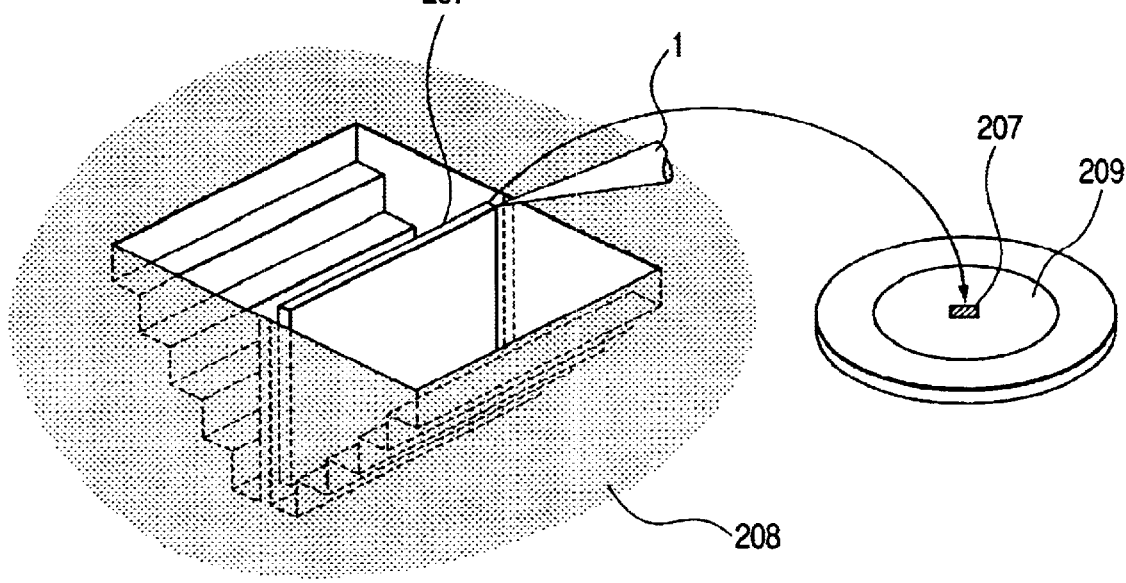
Figure 4:
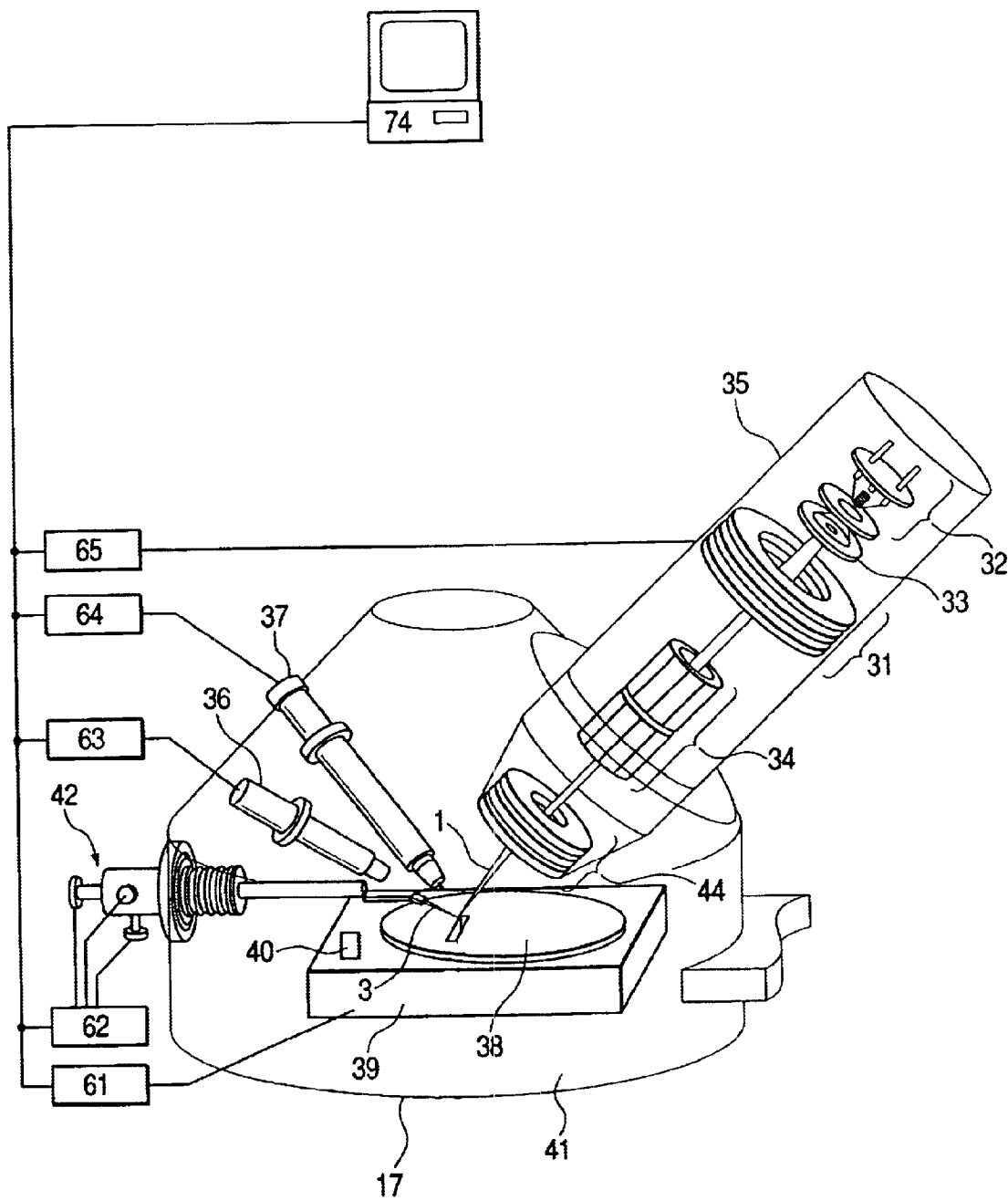
FIG. 4 is a configuration block diagram showing an embodiment of a sample fabricating apparatus according to the invention.

A schematic configuration of a sample fabricating apparatus as an embodiment of the invention will be describe by referring to FIG. 4.

A sample fabricating apparatus 17 has a vacuum chamber 41 in which an ion beam irradiating optical system 35 constructed by an ion source 32, a beam limiting aperture 33, an ion beam scanning electrode 34, an ion beam lens 31, and the like; a secondary electron detector 36 for detecting secondary electrons and secondary ions emitted from a sample irradiated with an FIB; a deposition-gas supplying source 37 for supplying an original material gas to form a deposition film in an ion beam irradiation area; the probe 3 attached at the tip of a manipulator 42; a specimen stage 39 on which a specimen base 38 such as a semiconductor wafer or a semiconductor chip is placed; a sample holder 40 for fixing a micro sample as a part extracted from the specimen base 38, and the like are disposed. In this case, the ion beam irradiating optical system 35 is mounted relative to the stage 39 so that the angle formed by an almost center axis of an objective lens 44 and the surface of the sample becomes almost 45 degrees. The specimen stage 39 has the function of turning around a line segment perpendicular to the surface of a sample as a rotation axis. As apparatuses for controlling the apparatus, a stage controller 61 mainly including an electric circuit and an arithmetic unit, a manipulator driver 62, an amplifier 63 for the secondary electron detector, a deposition gas controller 64, an FIB controller 65, a central processing unit 74, and the like are disposed. The central processing unit 74 has the function of recognizing the shape of a sample by performing an image process on a secondary electron image formed by secondary electrons generated from the sample irradiated with the FIB. The central processing unit 74 also has the function of irradiating a desired position in the sample shape with the FIB 1 by the FIB controller 65 on the basis of sample shape information.

An operation of the sample fabricating apparatus will now be described. First, ions released from the ion source 32 are emitted to the specimen base 38 via the beam limiting aperture 33, ion beam lens 31, and objective lens 44. The FIB 1 is narrowed so that its diameter becomes a few nm to about 1 micrometer on the sample. When the specimen base 38 is irradiated with the FIB 1, atoms constructing the surface of the sample are released to the vacuum by a sputtering phenomenon. By making a scan with the FIB 1 by using the ion beam scanning electrode 34, processing at a micrometer level to a sub-micrometer level can be performed. By irradiating the specimen base 38 with the FIB 1 while introducing a deposition gas into the specimen chamber, a deposition film can be formed. In such a manner, the specimen base 38 can be processed by skillfully using the sputtering or deposition with the FIB 1. The deposition film formed by the irradiation with the FIB 1 is used to connect the contact portion at the tip of the probe 3 and the sample or to fix the extracted sample to a sample holder 40. As can with the FIB 1 is performed, secondary electrons and secondary ions emitted from the sample are detected by the secondary electron detector 36, and the intensities of the detected secondary electrons and secondary ions are converted to the luminance of an image, thereby enabling the specimen base 38, the probe 3, and the like to be observed.

Figure 8A:
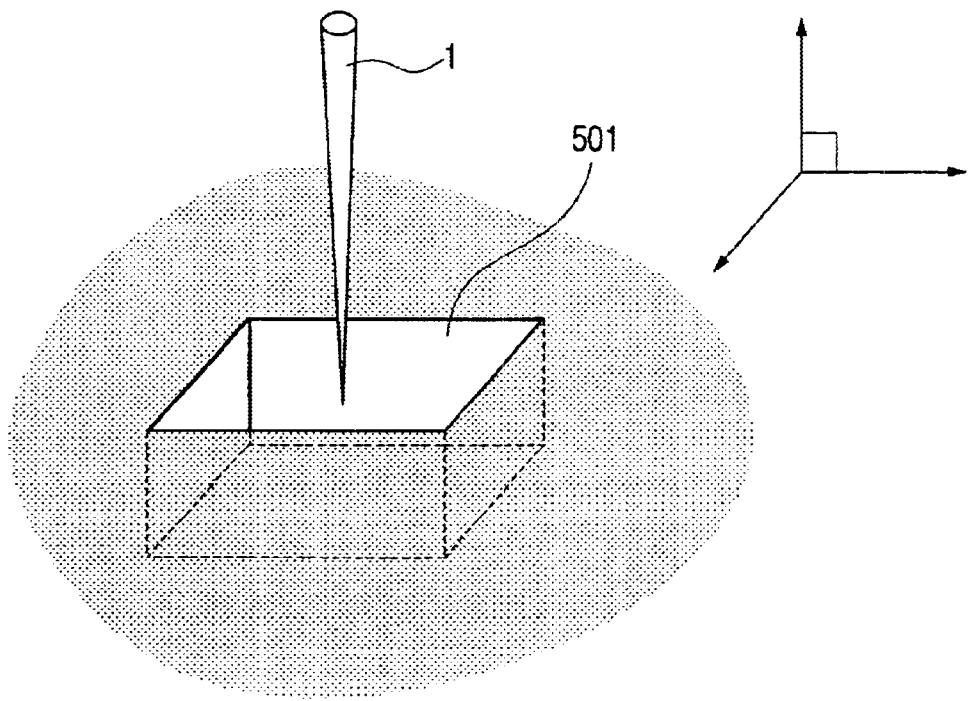
FIGS. 8(a) and 8(b) are supplementary diagrams for understanding of FIGS. 1(a) to 1(f).
Figure 8B:
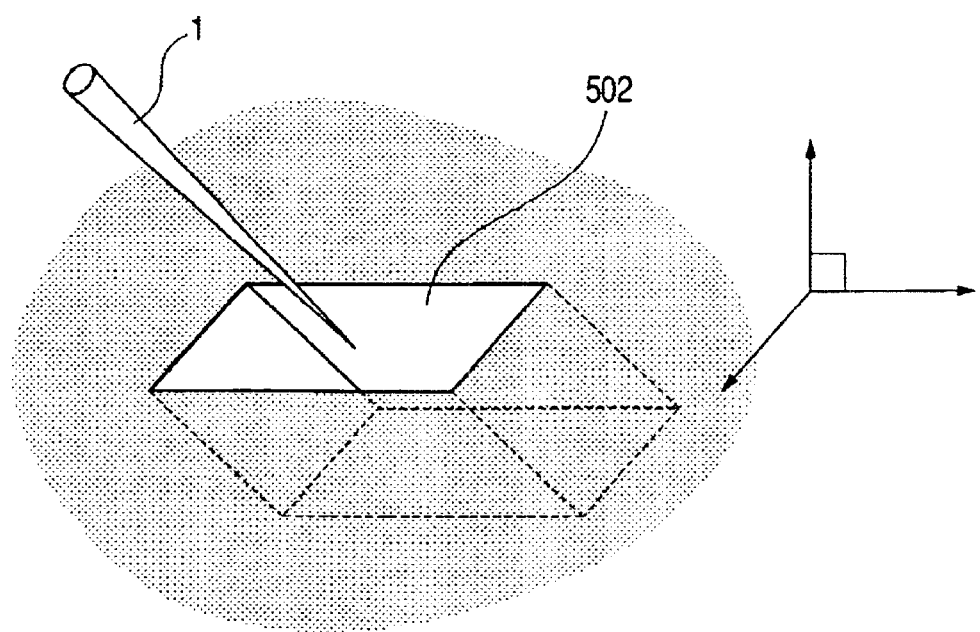
Figure 9A:
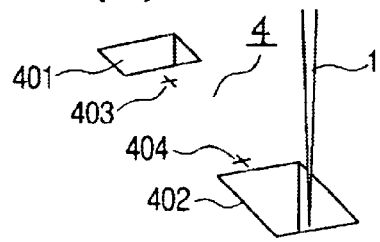
FIGS. 9(a) to 9(j) are diagrams for explaining a conventional TEM sample fabricating method and, particularly, an example using an FIB and carrying means.
Figure 9F:
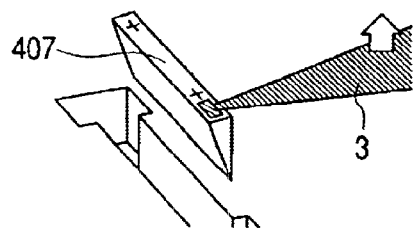
Figure 9B:
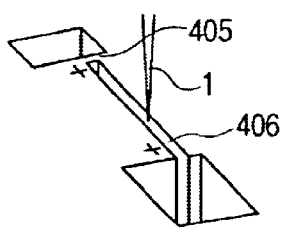
Figure 9G:
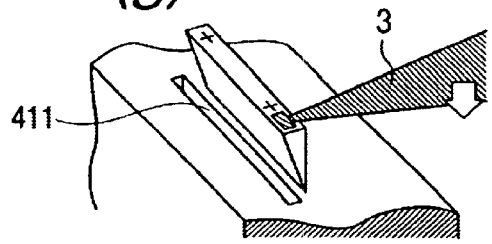
Figure 9C:
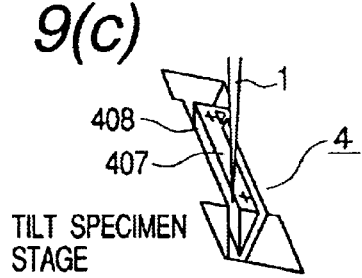
Figure 9H:
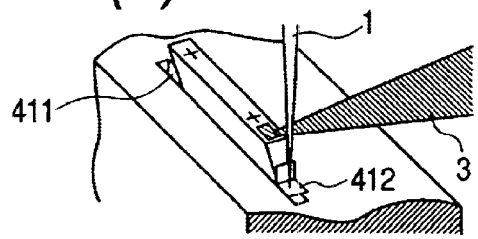
Figure 9D:
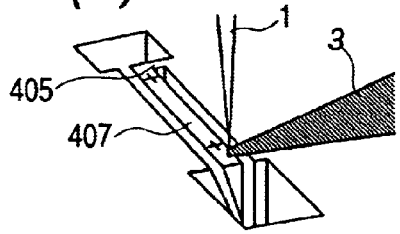
Figure 9I:
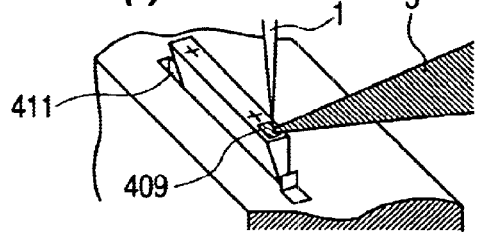
Figure 9E:
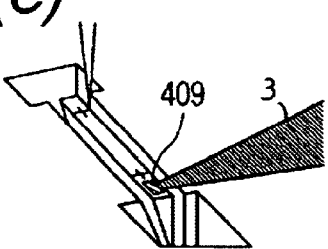
Figure 9J:
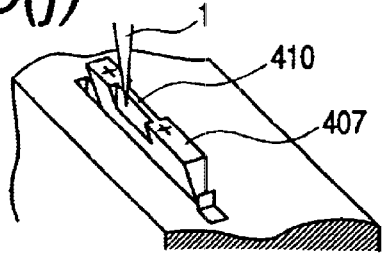

A sample fabricating method as an embodiment of the invention will now be described by referring to FIGS. 1(a) to 1(f). To understand FIGS. 1(a) to 1(f) as a supplement, refer to FIG. 8A showing a rectangular hole 501 fabricated when the FIB irradiation axis is normal to the surface of a sample and FIG. 8B showing a rectangular hole 502 fabricated when the FIB irradiation axis is at 45 degrees from the surface of a sample.

A sample is prepared as follows. First, a mark indicative of the fabrication position of a membrane for TEM observation and a protection film are formed on the base. Subsequently, a rectangle whose one side is in the direction of projection of the optical axis of an FIB to the base surface onto the surface of the sample is scanned with the FIB 1 on the specimen base to thereby form two rectangular holes 101 (FIG. 1(a)) having a depth of about 15 μm and tapered in the depth direction and an trench 102 similarly tapered in the depth direction (FIG. 1(b)). The FIB optical axis is tilted by 45 degrees from the surface of the sample. Subsequently, by using the axis perpendicular to the surface of the sample as a rotation axis, the sample is turned by about 180 degrees. By performing an image process on a secondary electron image formed by secondary electrons generated from the sample irradiated with the FIB 1, the two rectangular holes and the trench formed so far are recognized. The FIB irradiation position is controlled by the FIB controller 65 on the basis of the sample shape information, and a trench 103 similarly tapered in the depth direction is formed (FIG. 1(*c*)). Subsequently, by driving the probe controller, the tip of the probe 3 is made come into contact with the micro sample 6 on the base. After that, a deposition gas is supplied from the gas nozzle, an area including the tip portion of the probe 3 is locally irradiated with the FIB 1, and a deposition film 105 is formed to connect the portion separated from the base and the probe 3 which are in contact (FIG. 1(*d*)). By cutting a residual area 104 with the FIB 1, the micro sample 6 enters a state supported by the probe 3 connected (FIG. 1(*e*)). By moving the probe 3 upward, the micro sample 6 can be extracted (FIG. 1(*f*)). The following processes are similar to those in the conventional technique. Specifically, the specimen stage is operated while the probe is stopped above the specimen surface, thereby moving the micro sample onto a sample mesh. The micro sample is fixed to the sample mesh by using a deposition film. The probe is cut with the FIB so as to be separated from the micro sample. Finally, the observation area in the micro sample is thinned to a thickness of about 100 nm with the FIB, thereby completing the TEM sample.

Figure 5A:
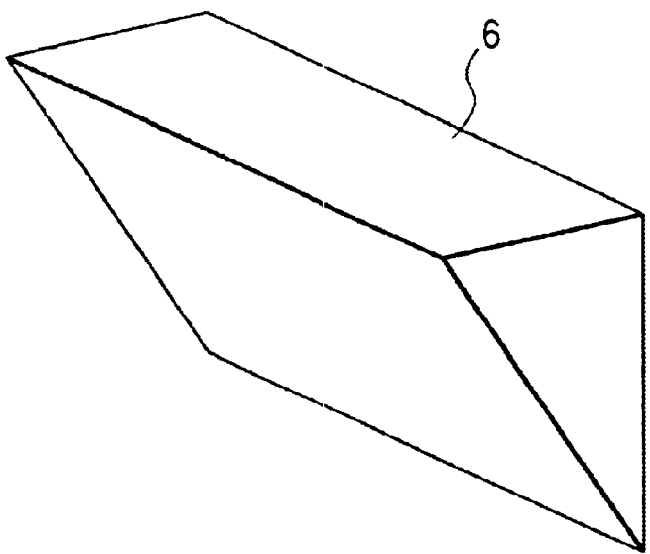
FIGS. 5(a) and 5(b) are diagrams of micro samples prepared by the sample fabricating method according to the invention.
Figure 5B:
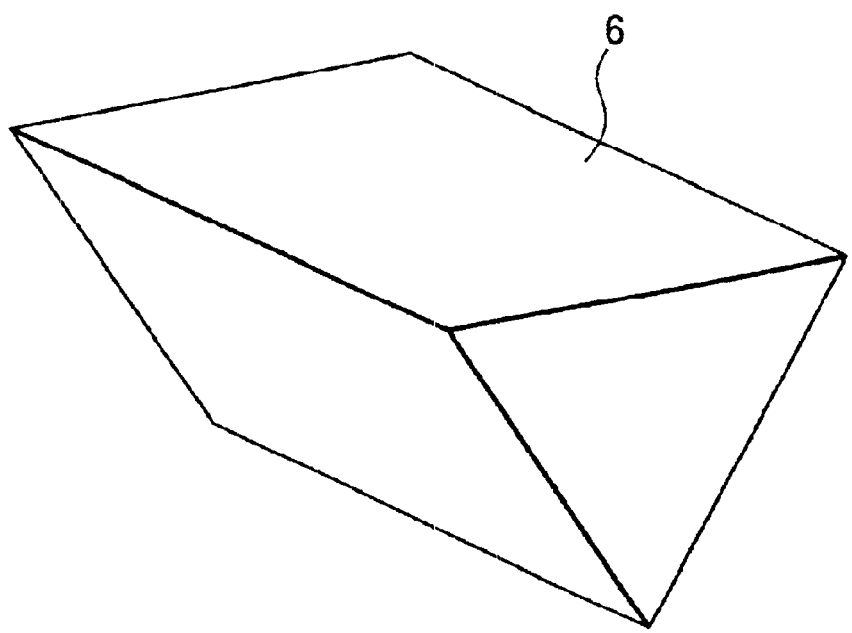

In the method, to form the trench tapered in the depth direction in FIG. 1(*c*), the sample is turned by about 180 degrees. Alternately, the trench may be also formed by turning the sample by about 90 degrees by using the axis perpendicular to the surface of the sample as a rotation axis. The shape of the micro sample in this case is as shown in FIG. 5(*a*). The shape of the micro sample formed by turning the sample by about 180 degrees is as shown in FIG. 5(*b*) The order of formation of the two rectangular holes (FIG. 1(*a*)), the trench (FIG. 1(*b*)) similarly tapered in the depth direction, and the trench (FIG. 1(*c*)) formed by turning the sample by about 180 degrees or 90 degrees is not limited.

In the embodiment, by performing image processing on a secondary electron image formed by secondary electrons generated from the sample irradiated with the FIB, the two rectangular holes and the trenches formed so far are recognized and the FIB irradiation position is controlled by the FIB controller on the basis of the sample shape information. The operation can be therefore automated and the burden on the operator can be lessened. However, it is not always necessary to use an image processor. The operator of the apparatus can control the FIB irradiation position by observing a secondary electron image on an image display.

In the case of forming a plurality of micro samples, each of the samples can be fabricated in accordance with the order. First, two rectangular holes 101 (FIG. 1(*a*)) having a depth of about 15 μm and tapered in the depth direction and the trench 102 (FIG. 1(*b*)) similarly tapered in the depth direction are formed in necessary positions in each of a plurality necessary number of samples. By using an axis perpendicular to the surface of the sample as a rotation axis, the sample is turned by about 180 degrees. Subsequently to the positioning of the samples, the trench 103 tapered in the depth direction is formed in each of the samples (FIG. 1(*c*)). The probe controller is driven to fabricate a plurality of micro samples 6 as TEM samples in accordance with the order by using the probe 3. In such a manner, the turning operation requiring relatively long time can be reduced. Thus, a plurality of samples can be fabricated with throughput higher than that in the case of fabricating each of the samples in accordance with the order.

In the foregoing embodiment, in the series of processes of separating the micro sample from the specimen base, the angle formed between the FIB and the sample surface is 45 degrees and unchanged. That is, the process of tilting the stage is not included. According to the embodiment, therefore, even when the function of tilting the specimen stage is omitted to reduce the size of the whole apparatus, preparation of a sample for analyzing, observing, or measuring a micro area by separating a micro sample from a sample or preparing the micro sample to be separated can be realized. Also in the case of the apparatus in which the specimen stage has the tilting function different from the embodiment, the invention is valid. The time required to tilt the stage is unnecessary, so that the sample preparation time becomes relatively shorter. A problem such that the surface of the sample cannot be observed before and after the specimen stage is tilted is reduced. In the embodiment, a micro sample is extracted from the specimen base at the time of forming a membrane for the TEM sample, so that the section of the micro sample can be observed in detail, and the section processing position can be controlled with high precision.

According to the embodiment, the sample fabricating apparatus for preparing a sample for analyzing, observing, or measuring a micro area by separating a micro sample from a sample or preparing the micro sample to be separated, which is suitable from the viewpoints that operations of the apparatus can be automated and the burden on the operator can be lessened is provided.

In the embodiment, the specimen stage is constructed by combining a stage which turns at a predetermined fixed angle and a stage which can be turned at an arbitrary angle. The stage which is turned at the fixed angle is turned by 180 degrees or 90 degrees as described above. The stage which is turned at an arbitrary angle is operated by adjusting a processing position on a sample or the like. Generally, the precision for determining the turn angle of the stage which turns at an arbitrary angle is at most 0.01 degree. As in the embodiment, in the case where fine positioning is necessary after the turn, precision is insufficient. However, in the stage having the function of only the turning at a specified fixed angle, the turn precision can be further increased. Therefore, the operation for turning the stage by a fixed angle to adjust the process position after the turn of 180 degrees or 90 degrees in the embodiment is suitable to shorten the time required for the positioning and to increase the throughput of preparing the sample.

In the embodiment, the FIB optical axis is set to 45 degrees from the surface of a sample. In the case of observing both the surface of a sample and a sample section by the irradiation with an FIB, the FIB irradiation angle is 45 degrees in both cases, and both of them can be observed under similar conditions. Thus, 45 degrees is suitable for separating a sample or preparing a sample to be separated. However, the angle is not limited to 45 degrees. At an angle smaller than 90 degrees, an affect of the invention can be obtained. When the FIB optical axis is tilted from the surface of a sample by an angle less than 30 degrees, a process area for separating a micro sample is enlarged and the sample surface is wasted. When the angle becomes 75 degrees or more, the angle from the surface of an actually processed wall face becomes nearly 90 degrees and the process depth for separating the micro sample increases. There are cases such that the process time becomes longer and, further, the micro sample cannot be separated. In order to separate a micro sample, therefore, the angle formed between the sample irradiation axis of a beam and the surface of the sample is preferably in a range from 30 degrees to 75 degrees.

Although the designing of the apparatus is simplified by setting the angle formed between an almost mechanical center axis of the objective lens in the focused ion beam irradiating system and the surface of the specimen base to 45 degrees so that the angle formed between the FIB optical axis and the surface of the sample becomes 45 degrees, even when the angle other than 45 degrees is set, the FIB optical axis can be tilted by 45 degrees from the sample surface by tilting the ion beam.

In the embodiment, a semiconductor wafer having a flat shape is used as an example of the sample. The invention is valid for, not necessarily a flat sample, but a sample of an arbitrary shape. In the above, the angle formed between the surface of a sample and the ion beam sample irradiation axis has been described. In the case of a sample of an arbitrary shape, it is sufficient to fix an angle with a face on which a sample is to be placed of the specimen stage to prepare a sample. For example, the invention can be also applied to what is called micro machining for separating a micro part from a sample in accordance with the invention and connecting the separated micro part with another micro part to thereby fabricate a fine mechanical structure, a fine device, or the like.

The sample fabricating apparatus suitable for carrying out the example has a structure in which an angle formed between an almost center axis of a mechanical column including a focused ion beam irradiating optical system and the face on which a sample is placed of the specimen stage is fixed and is characterized by including means for separating a requested portion in a sample and a probe for supporting the separated sample. In a semiconductor wafer having a flat shape as a sample, the sample placement face and the surface of a sample are parallel to each other. Obviously, the angle formed between the sample irradiation axis of the focused ion beam and the sample surface and the angle formed between the sample irradiation axis of the focused ion beam and the sample placement face of the specimen stage are the same.

In the embodiment, the sample is scanned with a focused ion beam. At this time, the angle of a focused ion beam incident on the sample slightly varies depending on the scan position, but the change in the incident angle of an ion beam in association with such scanning is not included in a change in the angle between the sample irradiation axis of the focused ion beam and the surface of the sample. That is, when the sample is scanned with the focused ion beam, it is assumed that the angle formed between the sample irradiation axis of the focused ion beam and the surface of the sample can be fixed. The sample irradiation axis of the focused ion beam denotes a center line of an ion beam incident on the surface of a sample when the scanning is stopped and there is no deflection by a scan electrode.

Second Embodiment

Another sample fabricating method as an embodiment of the invention will now be described by referring to FIGS. 6(a) to 6(d). A sample fabricating apparatus similar to the apparatus shown in FIG. 4 is used.

First, a mark indicative of the fabrication position of a membrane for TEM observation and a protection film are formed on a specimen base. A rectangle whose one side is in the direction of projection of the irradiation axis of an FIB to the base surface onto the surface of the sample is scanned with the FIB 1 on the specimen base to form two rectangular holes 301(FIG. 6(a)) having a depth of about 15 μm and tapered in the depth direction. In this case, a membrane between the two rectangular holes 301 is a sample as a target and the thickness of the membrane is about 100 nm. Subsequently, membrane both ends 302 are cut. By using the axis perpendicular to the surface of the sample as a rotation axis, the sample is turned by about 90 degrees. By performing an image process on a secondary electron image formed by secondary electrons generated from the sample irradiated with the FIB 1, the two rectangular holes 301 formed so far are recognized. The FIB irradiation position is controlled by the FIB controller 65 on the basis of the sample shape information, the bottom of a sample membrane 303 is cut with the FIB 1 as shown in FIG. 6(c) to thereby separate the sample membrane 303 from the specimen base. Alternately, the sample membrane 303 is not separated and the process is finished while leaving a residual area which can be broken by a little impact as a preparation for separation in a post process. After that, the specimen base is taken out from the sample fabricating apparatus and, by using static electricity of a glass stick 304 in atmosphere, the sample membrane 303 is moved from the specimen base onto a TEM sample holder. When the sample membrane 303 as a micro sample is not completely separated, an impact is given to the micro sample residual area by the glass stick 304, the sample membrane 303 is separated from the specimen base. After that, by similarly using the static electricity of the glass stick 304, the sample membrane 303 is moved from the specimen base onto the TEM sample holder. The method and apparatus for specimen fabrication for processing most of the outer shape of a micro sample with an ion beam without taking out the sample membrane 303 as a micro sample in the apparatus are also included in the invention.

Figure 6A:
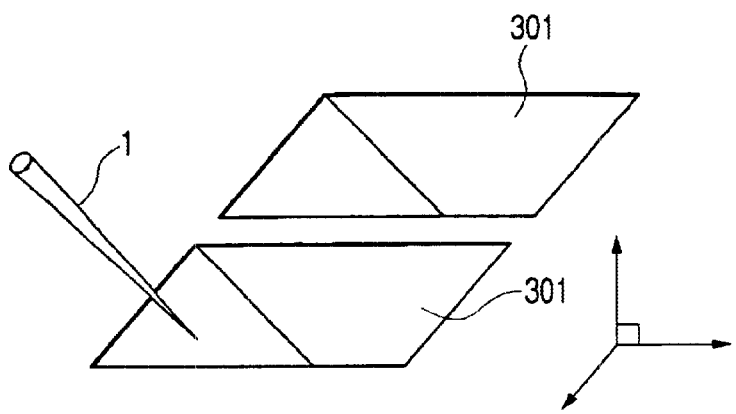
FIGS. 6(a) to 6(d) are diagrams for explaining an embodiment of the sample fabricating method according to the invention.
Figure 6B:
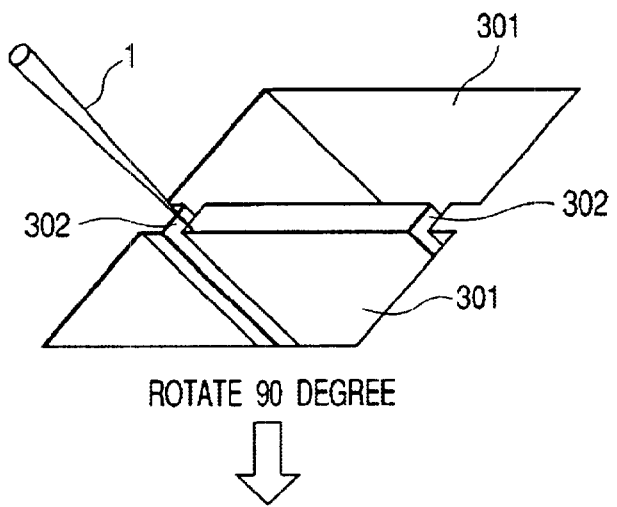
Figure 6C:
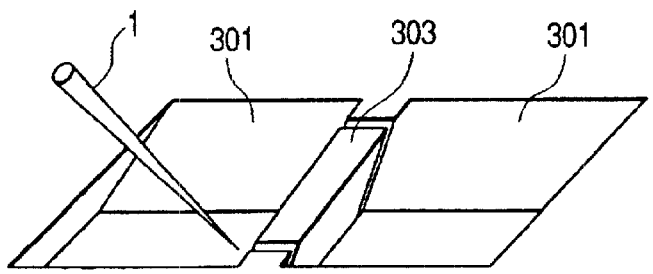
Figure 6D:
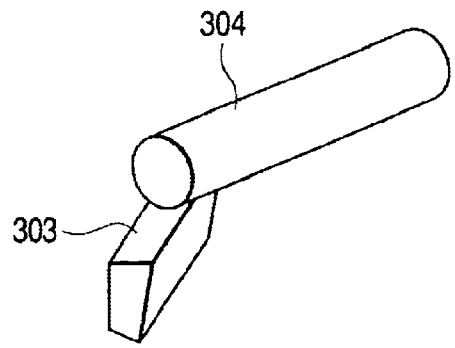

Although at least one of both sides of the sample membrane is cut in FIG. 6(b) before the sample is turned by about 90 degrees in the method, it may be cut after the turn. The order of fabrication of the two rectangular holes, cutting of both sides of the sample membrane, cutting of the bottom of the sample membrane, and the like is not limited.

Although image processing is used in the embodiment, in a manner similar to the first embodiment, the operator of the apparatus may observe a secondary electron image and control an FIB irradiation position.

In the foregoing embodiment, in the series of processes of separating a sample from a specimen base or preparing the sample to be separated, the angle formed between the FIB and the surface of a sample is 45 degrees and is unchanged. That is, the process of tilting the stage is not included. According to the embodiment, therefore, even if the function of tilting the specimen stage is eliminated to reduce the size of the whole apparatus, preparation of a sample for analyzing, observing, or measuring a micro area by separating a micro sample from the sample or preparing the micro sample to be separated can be realized. Also in the case of an apparatus in which the specimen stage has the tilting function in a manner different from the embodiment, the time required to tilt the stage is unnecessary and the sample fabrication time is made relatively short. A problem such that the surface of a sample cannot be observed before and after the specimen stage is tilted is also reduced. In the embodiment, a micro sample exists in the specimen base at the time of preparing a membrane for the TEM sample, so that the precision of the section processing position is relatively lower as compared with the first embodiment. However, the processes of operating the probe, forming an ion beam assist deposition film for adhering a probe and a micro sample, and the like are not included, so that the sample preparation time can be shortened.

In a manner similar to the first embodiment, the FIB irradiation angle is not always limited to 45 degrees. When the angle is smaller than 90 degrees, the effects of the invention can be obtained.

Third Embodiment

Figure 7:
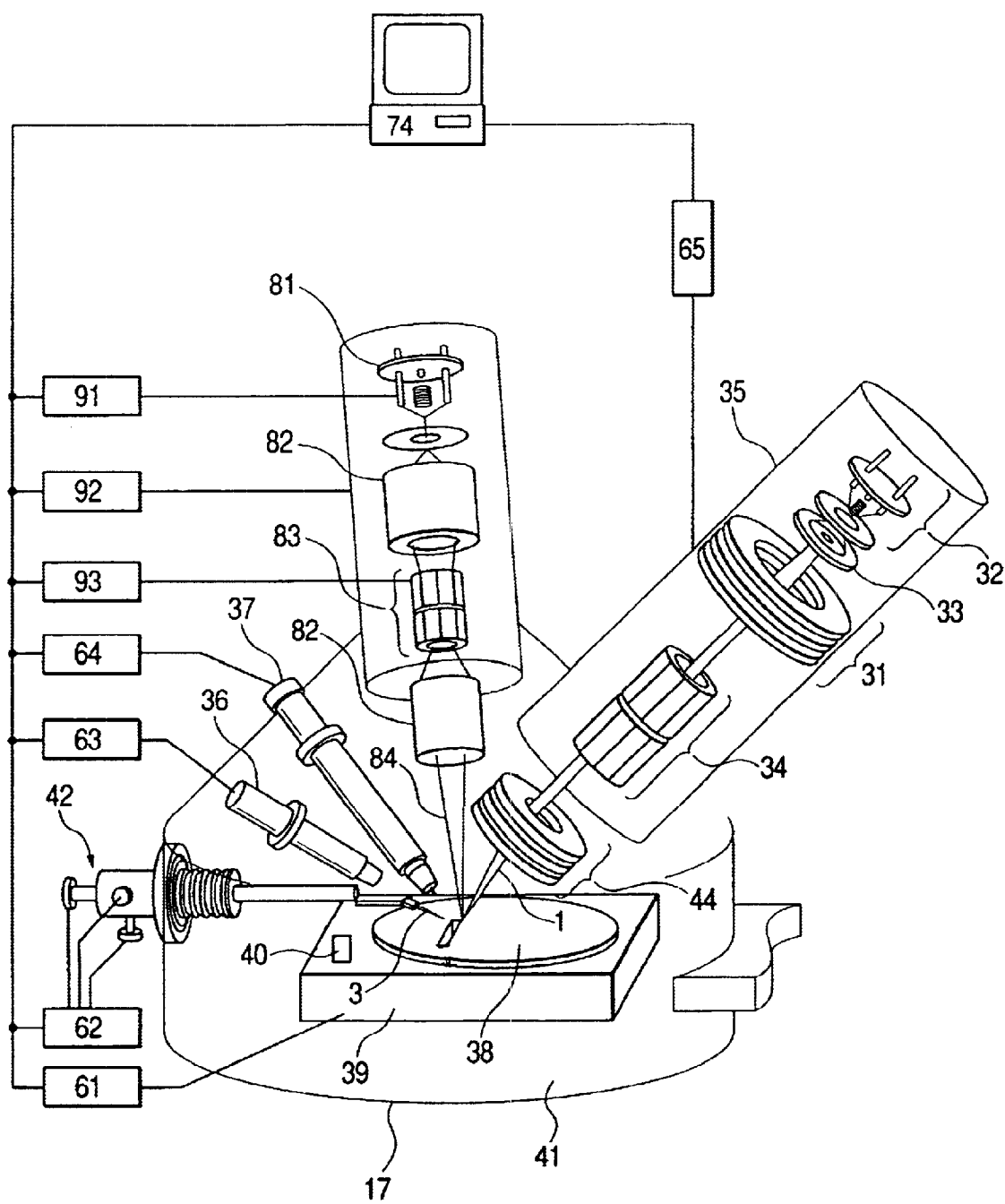
FIG. 7 is a configuration block diagram showing an embodiment of a sample fabricating apparatus according to the invention.

FIG. 7 is a schematic configuration diagram of a sample fabricating apparatus having an electron beam irradiating apparatus as an embodiment of the invention. A sample fabricating apparatus 17 has a vacuum chamber 41 in which an ion beam irradiating optical system 35, a secondary electron detector 36, a deposition-gas supplying source 37, a probe 3, a specimen stage 39, and the like are disposed in a manner similar to the sample fabricating apparatus of the second embodiment. Similarly, the ion beam irradiating optical system 35 is mounted relative to the stage 39 so that the angle formed between the FIB optical axis and the surface of the sample becomes 45 degrees. The specimen stage has the function of turning around a line segment perpendicular to the surface of a sample as a rotation axis. In the apparatus, an electron beam irradiating system constructed by a field emission electron gun 81 for emitting an electron beam, an electron beam lens 82, an electron scanning electrode 83, and the like is mounted. As apparatuses for controlling the apparatus, not only a stage controller 61, a manipulator driver 62, an amplifier 63 for the secondary electron detector, a deposition gas controller 64, and an FIB controller 65 but also an electron gun controller 91, an electron beam irradiating optical system controller 92, an electron beam scanning controller 93, a central processing unit 74, and the like are disposed. The central processing unit 74 has the function of recognizing the shape of a sample by performing an image process on a secondary electron image formed by secondary electrons generated from the sample irradiated with the FIB or an electron beam 84. The central processing unit 74 also has the function of irradiating a desired position of the sample shape with the FIB 1 by the FIB controller 65 on the basis of sample shape information and the function of irradiating a desired position of the sample shape with the electron beam 84 by the electron gun controller 91.

The operation of the ion beam irradiating optical system 35 is similar to that of the second embodiment. An operation of emitting an electron beam will now be described. An electron source of the electron beam irradiating apparatus is a field emission electron gun 81 and an arbitrary position in the specimen base 38 can be aimed by an electron scanning electrode 83. A process area 42 irradiated with an FIB can be also scanned and irradiated with the electron beam 84. For the operation, preparation is made as follows. First, the FIB 1 is condensed to a spot and emitted to a sample. The irradiation trace in the spot shape is scanned with the electron beam 84, secondary electrons are detected, and the spot-shaped irradiation trace is observed, thereby clarifying the relation between the irradiation position of the FIB 1 and the electron beam irradiation position. The relation is stored in the central processing unit 74. Therefore, on the basis of the stored information, the process position of the FIB 1 can be automatically irradiated with an electron beam, and the process status can be observed. All the above-described controls are performed by the central processing unit 74.

The sample fabricating method is similar to each of the methods described in the first and second embodiments. In the first and second embodiments, the image process on a secondary electron image formed by secondary electrons generated from a sample irradiated with an FIB is used for controlling the irradiation position of the FIB. However, in the apparatus of the third embodiment, a secondary electron image formed by secondary electrons generated from a sample irradiated with an electron beam can be used. When the sample irradiated with an electron beam is observed, as compared with preparation of a sample only with irradiation of the FIB, the number of damages in the surface of a sample is much smaller, and the sample preparation in shorter time can be realized.

According to the third embodiment, in a manner similar to the first and second embodiments, obviously, the sample fabricating apparatus for fabricating a sample for analyzing, observing, or measuring a micro area by separating a micro sample from a sample or preparing the micro sample to be separated, which is suitable from the viewpoint that the operation of the apparatus can be automated and the burden on the operator can be lessened is provided.

Fourth Embodiment

Figure 10A:
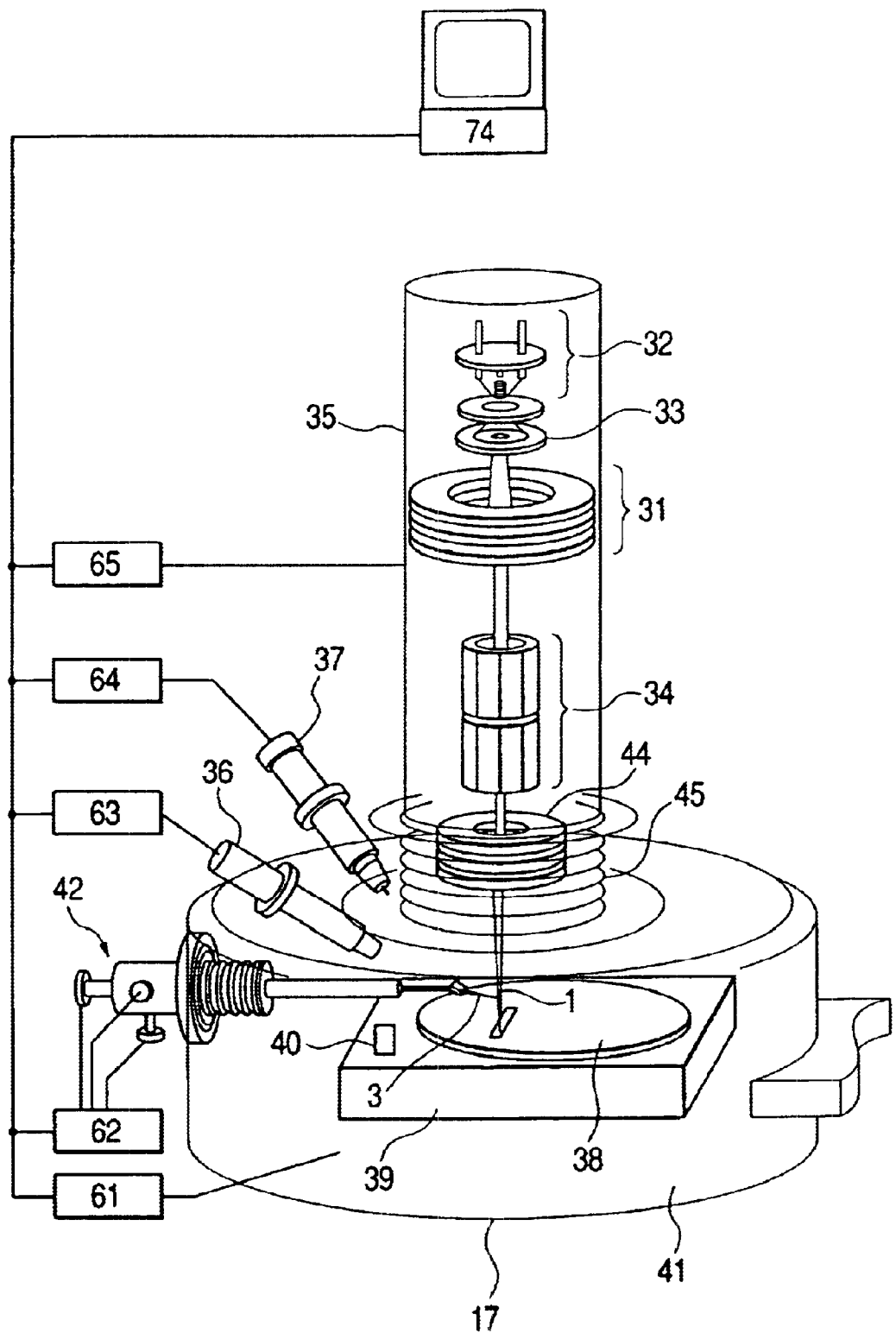
FIGS. 10(a) and 10(b) are configuration block diagrams each showing an embodiment of a sample fabricating apparatus according to the invention.
Figure 10B:
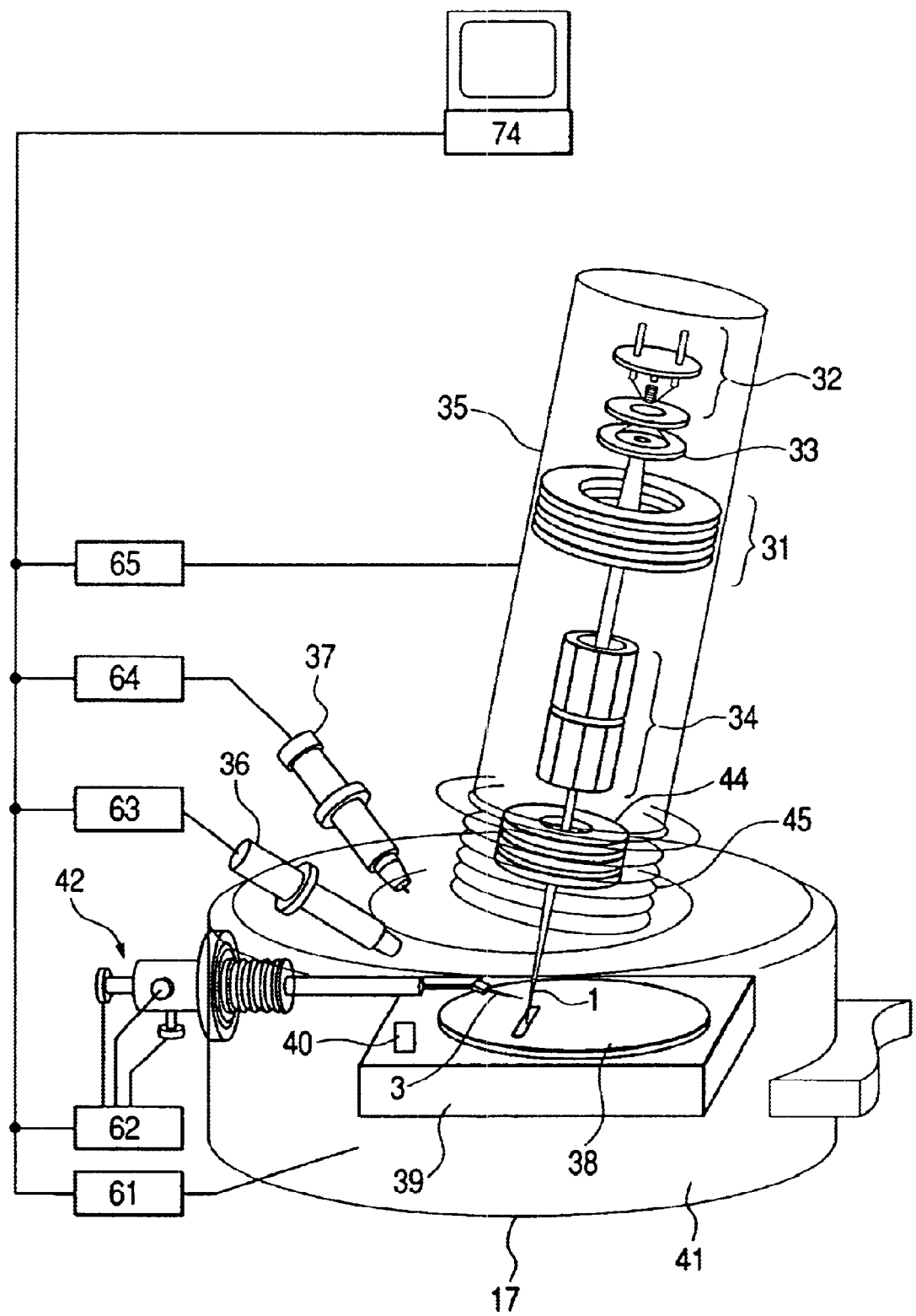

A schematic configuration diagram of a sample fabricating apparatus as an embodiment of the invention will be described by referring to FIGS. 10(a) and 10(b).

In the fourth embodiment, a focused ion beam tilting function capable of changing a focused ion beam incident direction by at least 15 degrees is realized by a mechanism of varying a tilt angle with respect to a specimen stage of a mechanical column including the focused ion beam irradiating system.

A sample fabricating apparatus 17 has a vacuum chamber 41 in which an ion beam irradiating optical system 35 constructed by an ion source 32, a beam limiting aperture 33, an ion beam scanning electrode 34, an ion beam lens 31, and the like; a secondary electron detector 36 for detecting secondary electrons and secondary ions emitted from a sample irradiated with the FIB; a deposition-gas supplying source 37 for supplying an original material gas to form a deposition film in an ion beam irradiation area; a probe 3 attached at the tip of a manipulator 42; a specimen stage 39 on which a specimen base 38 such as a semiconductor wafer or a semiconductor chip is placed; a sample holder 40 for fixing a micro sample as a part extracted from the specimen base 38, and the like are disposed. The ion beam irradiating optical system 35 is constructed so as to set the angle of the FIB irradiation axis tilted from the specimen base surface in a range from 75 degrees to 90 degrees. In the embodiment, the ion beam irradiating optical system 35 and the vacuum chamber 41 are connected to each other via a bellows 45, and deformation of the bellows is used. FIG. 10(a) shows a state where the angle of the FIB irradiation axis from the surface of the specimen base is 90 degrees, and FIG. 10(b) shows a state where the angle is 75 degrees. As apparatuses for controlling the apparatus, a stage controller 61 mainly including an electric circuit and an arithmetic unit, a manipulator driver 62, an amplifier 63 for the secondary electron detector, a deposition gas controller 64, an FIB controller 65, a central processing unit 74, and the like are disposed.

Figure 12A:
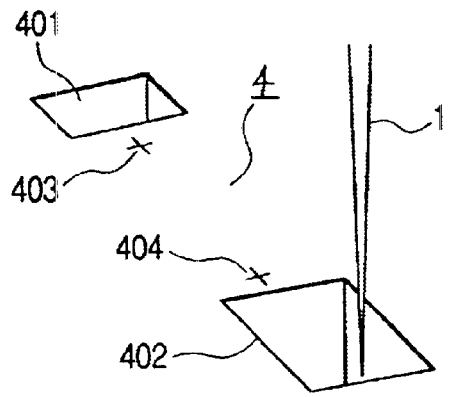
FIGS. 12(a) to 12(d) are diagrams for explaining a sample preparing procedure of the embodiment.
Figure 12B:
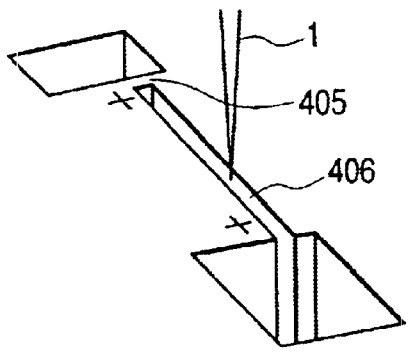
Figure 12C:
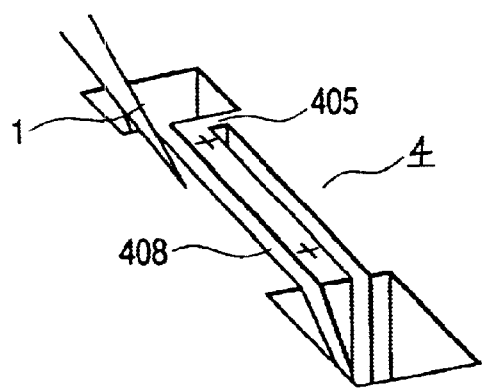
Figure 12D:
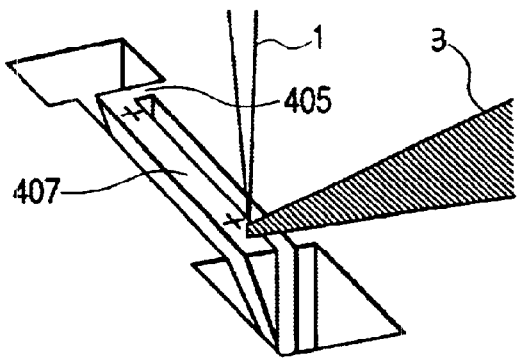

FIGS. 12(a) to 12(d) show a sample fabricating method according to the fourth embodiment. Conventionally, the tapered trench 408 is formed by tilting the specimen stage and obliquely irradiating the surface of a sample with the FIB 1. In place of tilting the specimen stage, it is sufficient to tilt the ion beam irradiating optical system 35 as shown in FIG. 10(b) and form the tapered trench 408 as shown in FIG. 12(c). The other processes are similar to those in the conventional technique.

According to the embodiment, the sample fabricating apparatus capable of fabricating a sample for analyzing, observing, or measuring a micro area by separating a micro sample including are quested specific area from a sample of an electronic part such as a semiconductor wafer, a semiconductor device, or the like and preparing the micro sample to be separated without tilting the specimen stage is realized by a focused ion beam tilting function capable of changing a focused ion beam incident direction by at least 15 degrees. In particular, according to the embodiment, since the focused ion beam incident angle can be selected in preparation of a sample, various sample fabricating methods and sample shapes can be realized.

Fifth Embodiment

Figure 11:
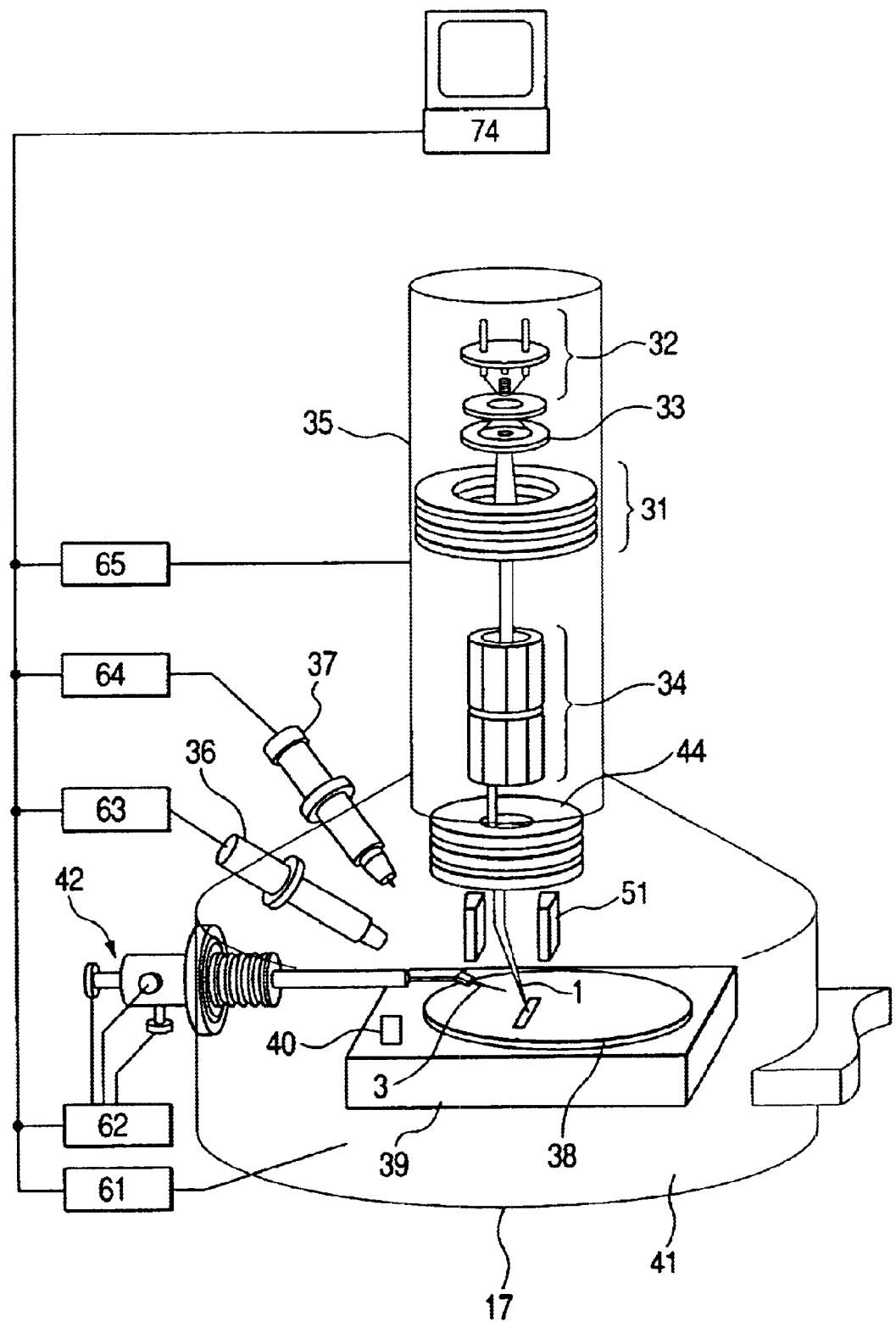
FIG. 11 is a configuration block diagram showing an embodiment of a sample fabricating apparatus according to the invention.

A schematic configuration of a sample fabricating apparatus as an embodiment of the invention will now be described by referring to FIG. 11. In the fifth embodiment, a focused ion beam deflecting function capable of changing a focused ion beam incident direction at least by 15 degrees is realized by electric deflection.

A sample fabricating apparatus 17 has a vacuum chamber 41 in which an ion beam irradiating optical system 35, a secondary electron detector 36, a deposition-gas supplying source 37, a probe 3, a specimen stage 39, a sample holder 40, and the like are disposed in a manner similar to the third embodiment. In this case, a deflector 51 for changing angle is further disposed between the objective lens 44 and the specimen stage 39. By an ion beam deflecting action of the deflector 51, the angle of the FIB optical axis with respect to the specimen base surface can be set so as to be changed in a range from 75 degrees to 90 degrees. As apparatuses for controlling the apparatus, a stage controller 61 mainly including an electric circuit and an arithmetic unit, a manipulator driver 62, an amplifier 63 for the secondary electron detector, a deposition gas controller 64, an FIB controller 65, a central processing unit 74, and the like are disposed.

The sample fabricating method according to the fifth embodiment is shown in FIGS. 12(a) to 12(d). Conventionally, the tapered trench 408 is formed by tilting the specimen stage to obliquely irradiate the surface of a sample with the FIB 1. In place of tilting the specimen stage, it is sufficient to tilt the ion beam irradiation axis relative to the sample as shown in FIG. 11 by the deflector 51 for changing angle and form the tapered trench 408 as shown in FIG. 12(c). The other processes are similar to those in the conventional technique.

According to the fifth embodiment, the sample fabricating apparatus capable of fabricating a sample for analyzing, observing, or measuring a micro area by separating a micro sample including a requested specific area from a sample of an electronic part such as a semiconductor wafer, a device, or the like or preparing the micro sample to be separated is realized by an electric deflecting action of the deflector for changing angle capable of changing a focused ion beam incident direction by at least 15 degrees. In particular, the mechanical apparatus configuration is simplified, the apparatus manufacturing cost can be reduced and, further, the focused ion beam incident angle can be selected in preparation of a sample. Thus, various sample fabricating methods and sample shapes can be realized.

Sixth Embodiment

Figure 13:
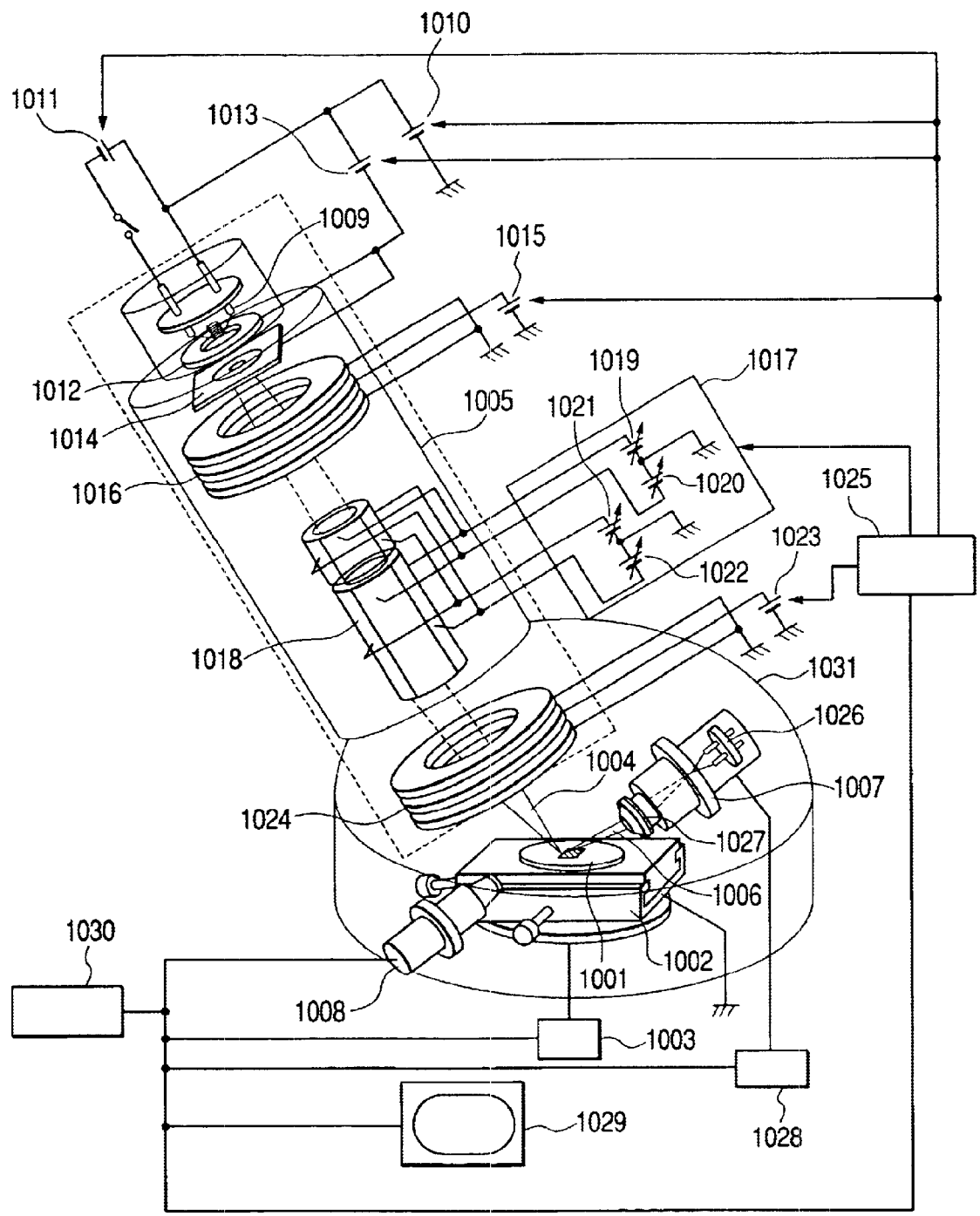
FIG. 13 is a general configuration diagram showing an embodiment of a sample fabricating apparatus according to the invention.

FIG. 13 is a configuration block diagram showing an embodiment of a sample fabricating apparatus according to the invention.

The sample fabricating apparatus has: a specimen stand 1002 which is movable but is not tilted on which a sample 1 such as a semiconductor wafer or a semiconductor chip is placed; a specimen-stage position controller 1003 for controlling the position of the specimen stand 1002 to specify the position of observing and processing the sample 1001; an ion-beam irradiating optical system 1005 for irradiating a peripheral portion of the observation position of the sample 1001 with an ion beam 1004 to form a hole for observation; an electron-beam irradiating optical system 1007 for emitting an electron beam 1006 for observing the peripheral portion of the sample 1001; and a secondary-electron detector 1008 for detecting secondary particles (for example, secondary electrons) from the sample 1001.

The configuration of the ion-beam irradiating optical system 1005 is as follows. An acceleration voltage with respect to the ground potential is applied to an ion source 1009 for generating ions by a power source 1010 for acceleration voltage. When emission of ions of the ion source 1009 is unstable, Joule's heating is performed by a power source 1011 for Joule's heating to improve the state of the ion source 1009. In an extractor 1012 for generating an ion extracting electric field, an extraction voltage is applied from an extractor power source 1013 to the ion source 1009. Flare of the extracted ion beam is limited by an aperture 1014. The aperture 1014 has the same potential as that of the extractor 1012. An ion beam passed through the aperture 1014 is condensed by a condenser lens 1016 to which a condensing voltage is applied by a condenser-lens power source 1015.

The condensed ion beam scans while being deflected by a deflector 1018 to which a deflector power source 1017 is applied. The deflector power source 1017 is constructed by power sources 1019 and 1020 for deflection in the X direction and power sources 1021 and 1022 for deflection in the Y direction. Potentials Vx/2 and Vx/2 of the same absolute value and opposite polarities are applied to counter electrodes in the X direction in the power sources 1019 and 1020. Potentials Vy/2 and Vy/2 are similarly set in the Y direction for the power sources 1021 and 1022. The deflected ion beam is condensed onto the surface of the sample 1001 by an objective lens 1024 to which an objective voltage is applied from an objective-lens power source 1023.

The power source 1010 for acceleration voltage, extractor 1013, condenser-lens power source 1015, deflector power source 1017, and objective-lens power source 1023 are controlled by a controller 1025 for ion-beam irradiating optical system. The optical axis of the ion beam of the ion-beam irradiating optical system 1005 is tilted relative to the surface of the sample 1.

The electron-beam irradiating optical system 1007 is constructed by an electron source 1026 for generating electrons, a deflector 1027 for deflecting and scanning an electron beam, and the like.

The controller 1025 for ion-beam irradiating optical system, specimen-stage position controller 1003, a controller 1028 for electron-beam irradiating optical system for controlling the electron-beam irradiating optical system 1007, a monitor 1029 for displaying information detected by the secondary-electron detector 1008, and the like are controlled by a central processing unit 1030. The specimen stage 1002, ion-beam irradiating optical system 1005, electron-beam irradiating optical system 1007, secondary-electron detector 1008, and the like are disposed in a vacuum chamber 1031.

Figure 14:
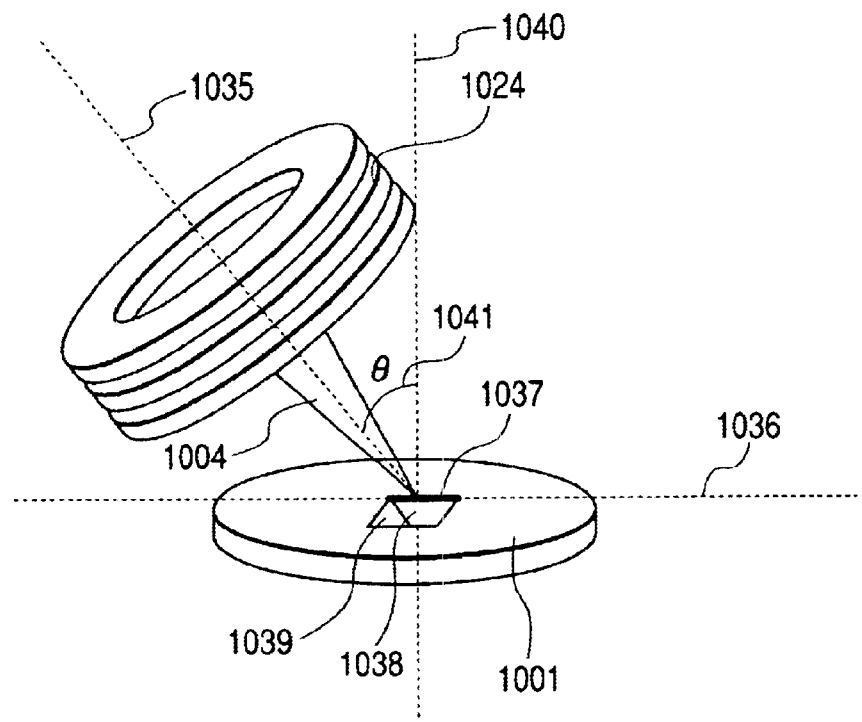
FIG. 14 is a diagram showing an example of forming a section with an ion beam emitted in an oblique direction.

FIG. 14 shows an example of processing a sample in the ion-beam irradiating optical system tilted for observing a section. In the configuration, an ion-beam irradiating optical axis 1035 is tilted from an axis 1040 perpendicular to the surface of the sample 1001. A tilt angle 1041 is set to an angle θ larger than 0° and smaller than 90°. 1036 denotes an optical-axis projected line which is the ion-beam irradiating optical axis 1035 projected on the surface of the sample. A processed hole 1039 is formed here to observe a formed section 1038. It is now assumed that a requested-section edge 1037 as a cross line of the formed section 1038 and the sample surface is parallel to the optical-axis projected line 1036 as shown in FIG. 14.

Figure 15:
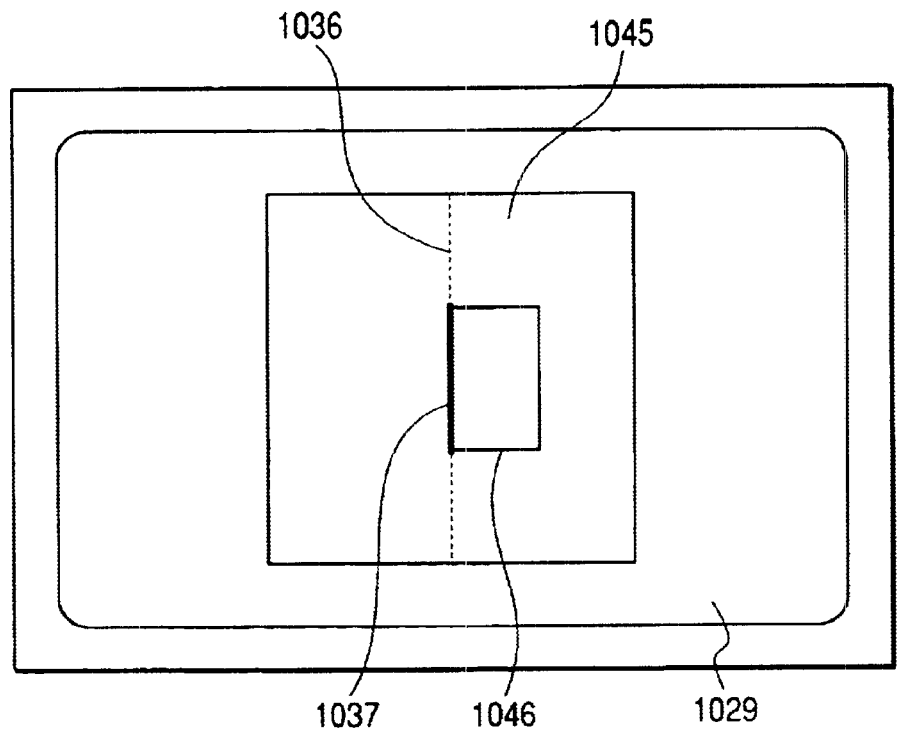
FIG. 15 is a diagram showing a section process setting screen on a secondary electron image.

At this time, the ion beam process setting is made by, as shown in FIG. 15, setting an ion-beam scan area 1046 on a secondary electron image 1045 in the monitor 1029. In this case, the requested-section edge 1037 is parallel to the optical-axis projected line 1036 (imaginary line which does not exist on the secondary electron image).

Figure 16:
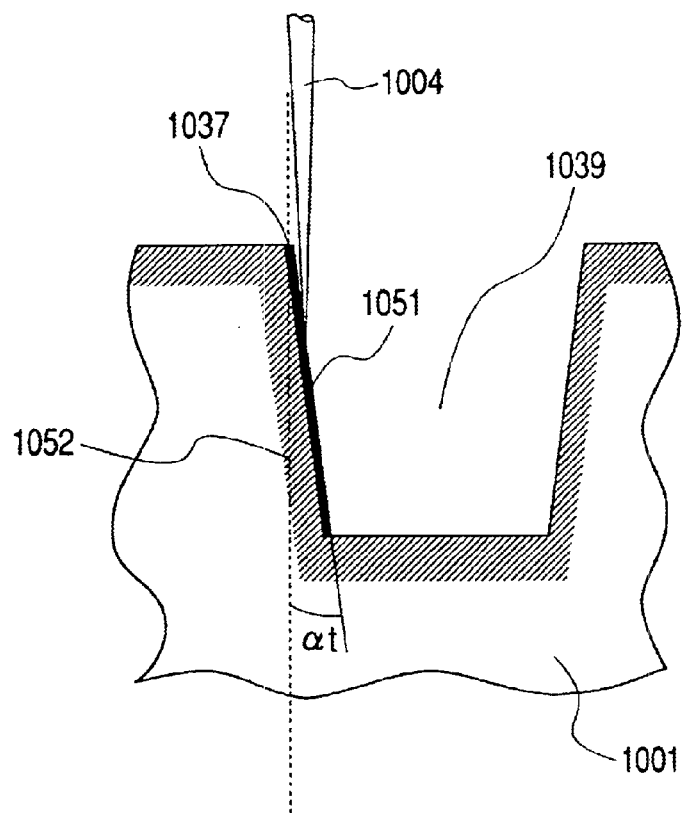
FIG. 16 is a diagram showing a section formed by emitting a parallel ion beam with respect to a requested section.

FIG. 16 shows a sample processed section in this case. In this case, the ion beam 1004 is emitted in parallel with a requested section 1052 to form the processed hole 1039. If ideal processing is realized, the formed section coincides with the requested section 1052. However, in reality, there are an influence of the ion beam flare, re-deposition, and the like, a section 1052 having a process taper angle αt is formed. Consequently, a positional deviation occurs with the distance in the depth direction, and there is the possibility that the accurate section cannot be observed, so that the following improvement is necessary.

Figure 17:
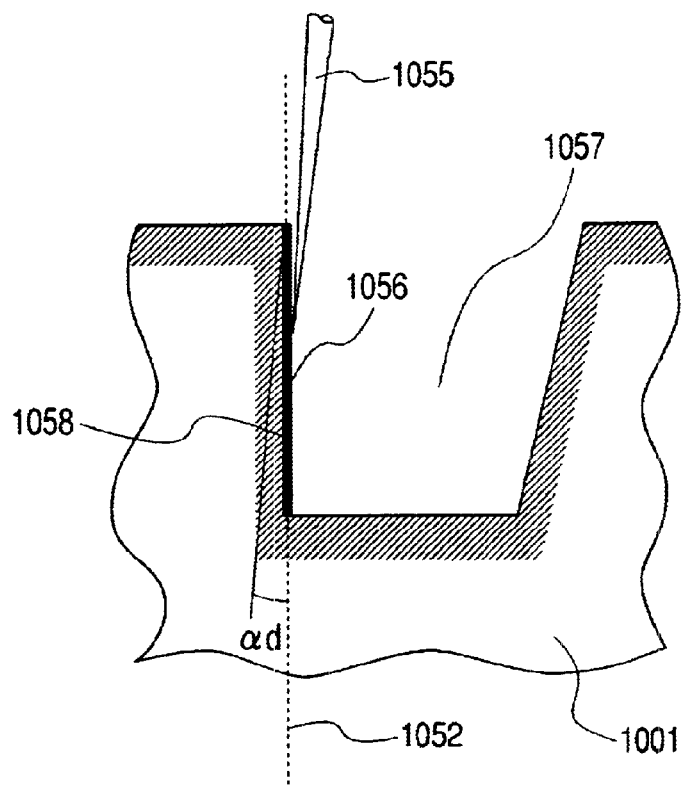
FIG. 17 is a diagram showing a section formed by emitting a tilted ion beam with respect to a requested section.

As shown in FIG. 17, when an ion beam 1055 is emitted while being tilted only by a tilt angle corresponding to the taper angle to form a processed hole 1054, a section 1056 is formed accurately in the position of the requested section 1052. In other words, it is sufficient to adjust the set section depression angle αd of a set section 1058 so as to coincide with the tilt angle αt corresponding to the taper angle in FIG. 16.

Figure 18A:
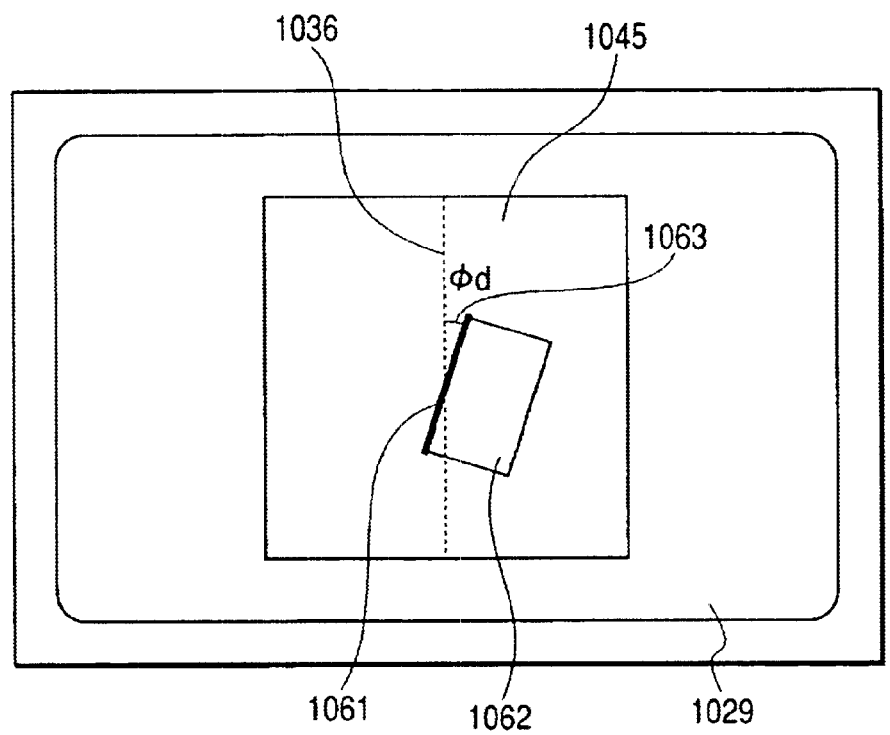
FIGS. 18(a) and 18(b) are diagrams each showing a section process setting screen on a secondary electron image at the time of irradiating a tilted ion beam.
Figure 18B:
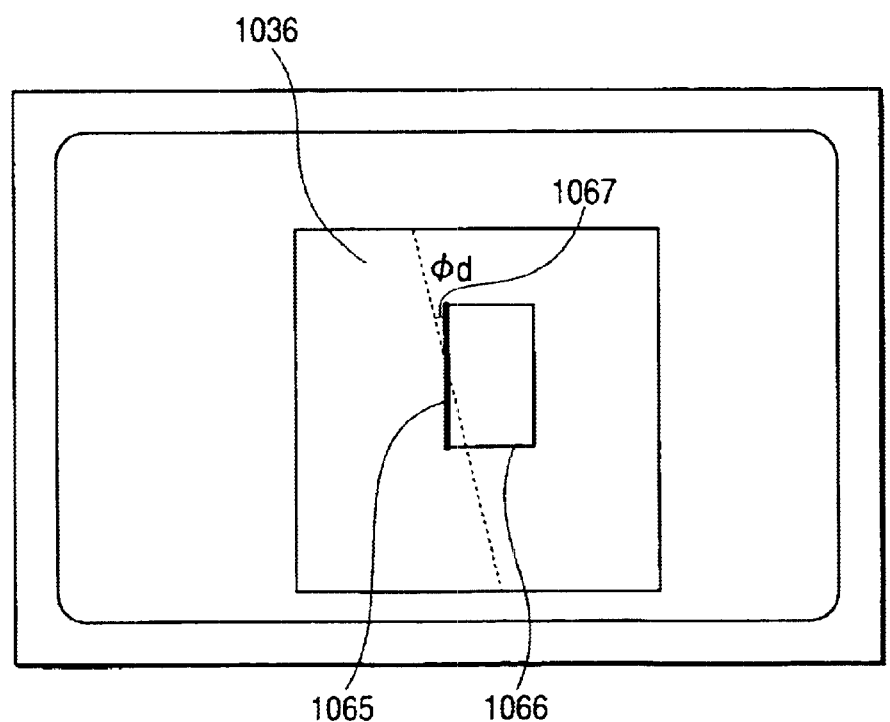

In order to realize the tilting by the not-tilting specimen stage, process setting shown in FIGS. 18(a) and 18(b) is made. In FIG. 18(a), setting is made so that a deflection scan area end 1061 (which is a set-section edge) of an ion-beam scan area 1062 forms a rotation angle 1063 for fabrication (in this case, expressed as φd) with respect to the optical-axis projected line 1036. As shown in FIG. 18(b), it is also possible to turn the whole secondary electron image 1045 by φd and display the turned image. In this case, the imaginary optical-axis projected line 1036 is turned by φd. An ion-beam scan area 1066 and a deflection scan area end (which is a set-section edge) 1065 are seen to be perpendicular on the secondary electron image 1045 in a manner similar to FIG. 15. Consequently, it is easier for the operator to make the fabrication setting. φd is calculated by the controller 1025 for ion-beam irradiating operation system by Formula 1 to thereby automatically set the scan of the deflector 1018.

$$\phi_d = \arctan\left(\frac{\tan\alpha_d}{\sqrt{(\sin\theta)^2 - (\tan\alpha_d \times \cos\theta)^2}}\right) \quad \text{Formula 1}$$

Since the ion beam optical axis tilt angle θ is determined in the apparatus, the rotation angle φd of fabrication setting with respect to the set section depression angle αd is unconditionally determined. In this case, −θ≦αd≦+θ is satisfied.

Figure 19:
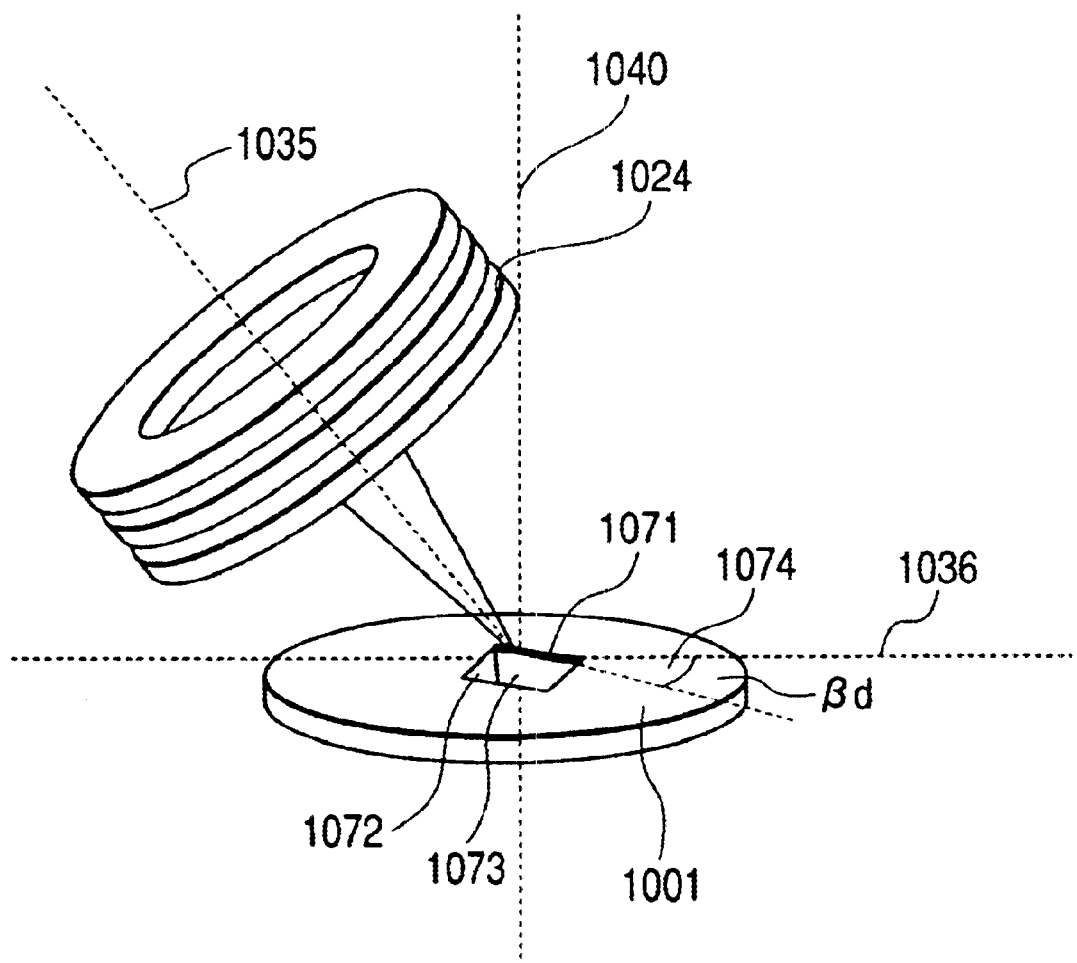
FIG. 19 is a diagram showing a section formed with a tilted ion beam.

FIG. 19 shows the process at this time. A set-section edge 1071 of a processed hole 1072 is deviated from the optical-axis projected line 1036 by an angle 1074 (expressed as a rotation angle βd of set-section edge). βd is expressed by Formula 2.

$$\beta_d = \arcsin\left(\frac{\tan\alpha_d}{\tan\theta}\right) \quad \text{Formula 2}$$

The relation between βd and φd is simply expressed as Formula 3.

$$\beta_d = \arctan(\cos\theta \times \tan\phi_d) \quad \text{Formula 3}$$

Figure 20A:
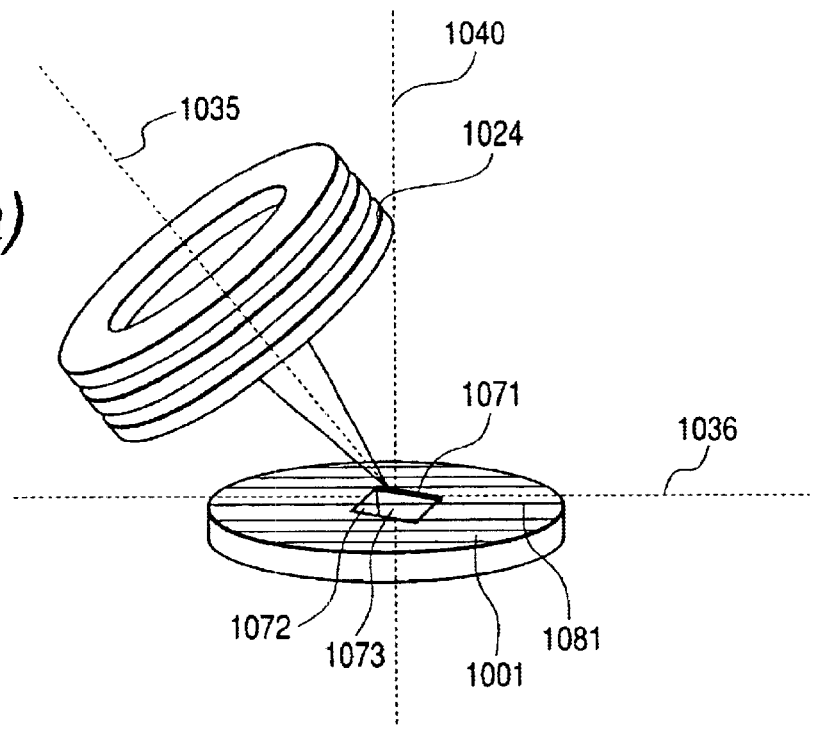
FIGS. 20(a) and 20(b) are diagrams each showing turning of a sample to make a structure in which a section is formed coincide with process setting.
Figure 20B:
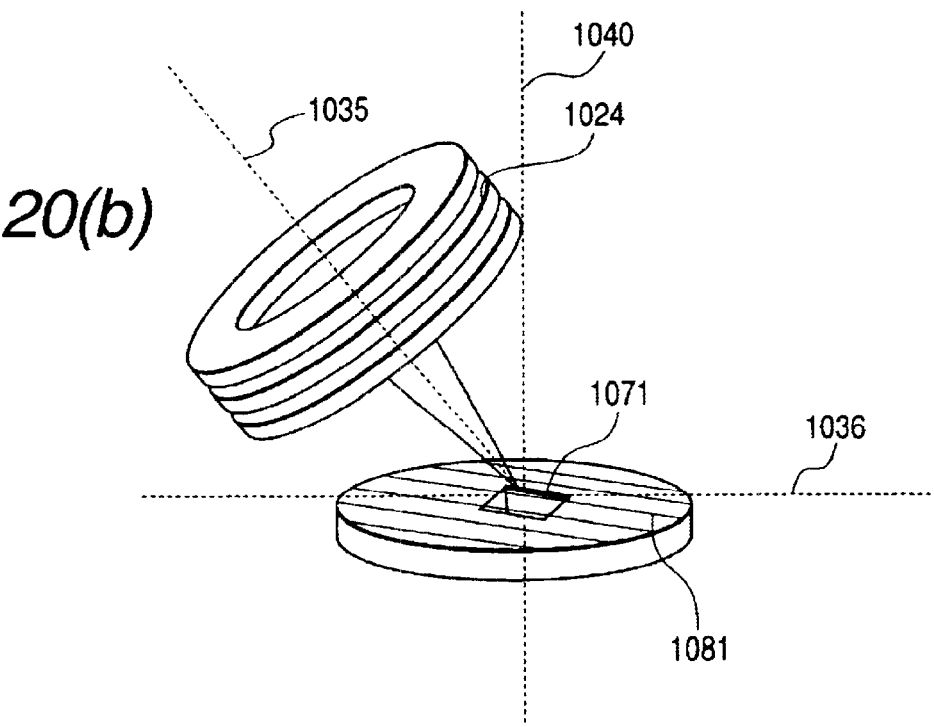

That is, as shown in FIG. 20(a) in FIG. 15 showing the secondary electron image in the case where the process rotation angle φd is 0°, when the state where a direction 1081 of the section processed structure is parallel to the optical-axis projected line 1036 is a turn reference (0° in this case) of the specimen stage 3, as shown in FIG. 20B, when the specimen stage is turned by βd, the set-section edge 1071 coincides with the direction 1081 of section processed structure, and a requested observation section can be prepared.

As described above, since the process rotation angle φd is determined by the set-section depression angle αd, the specimen stage rotation angle βr determined from the rotation angle βd of the set-section edge is also unconditionally determined with respect to the set-section depression angle αd. Consequently, by calculating Formula 2 by a sample position controller 1018, turning of the specimen stage in the direction of the structure from which a section is extracted can be automatically controlled.

Figure 21:
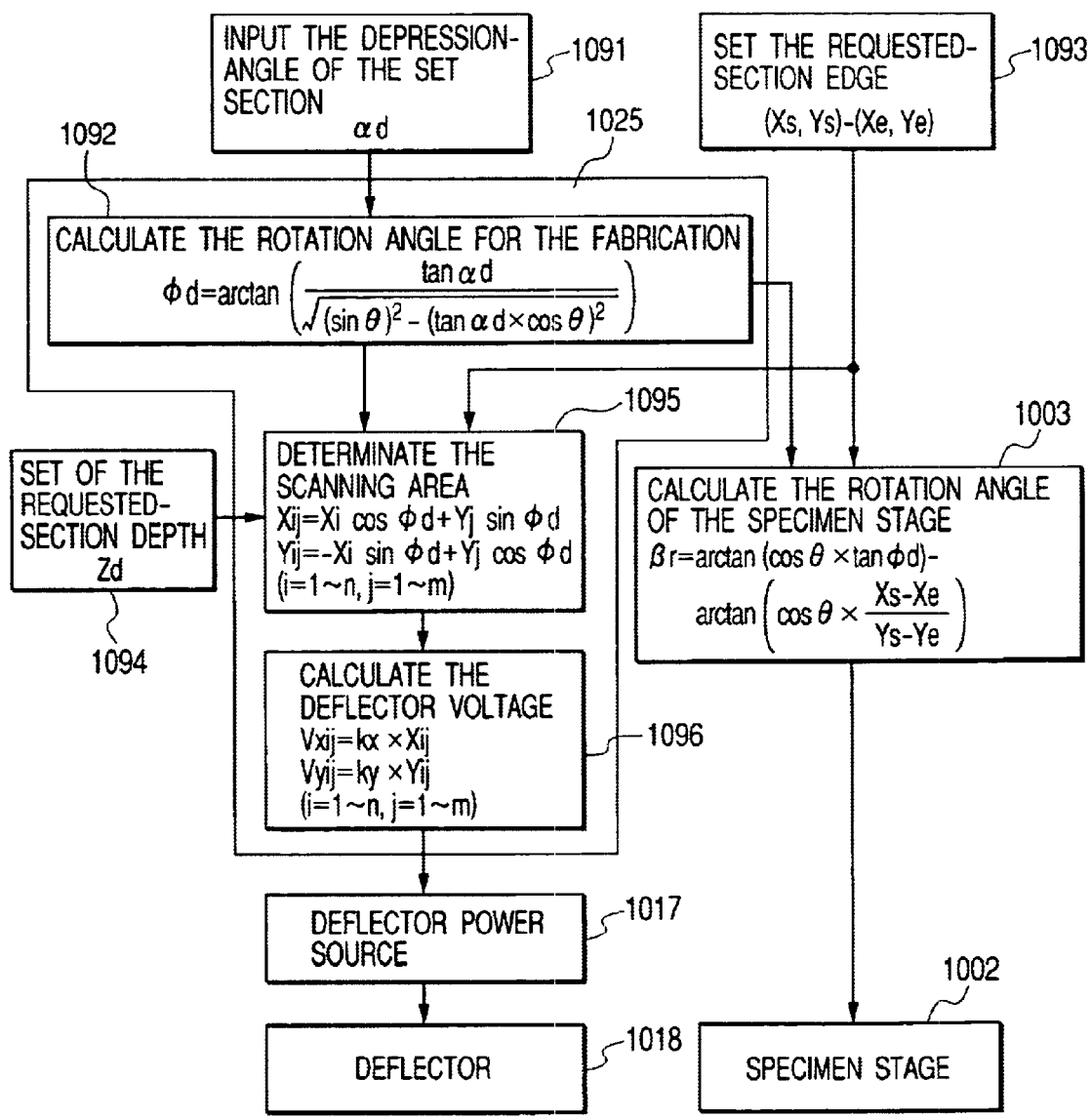
FIG. 21 is a flow chart of process setting in the invention.
Figure 22A:
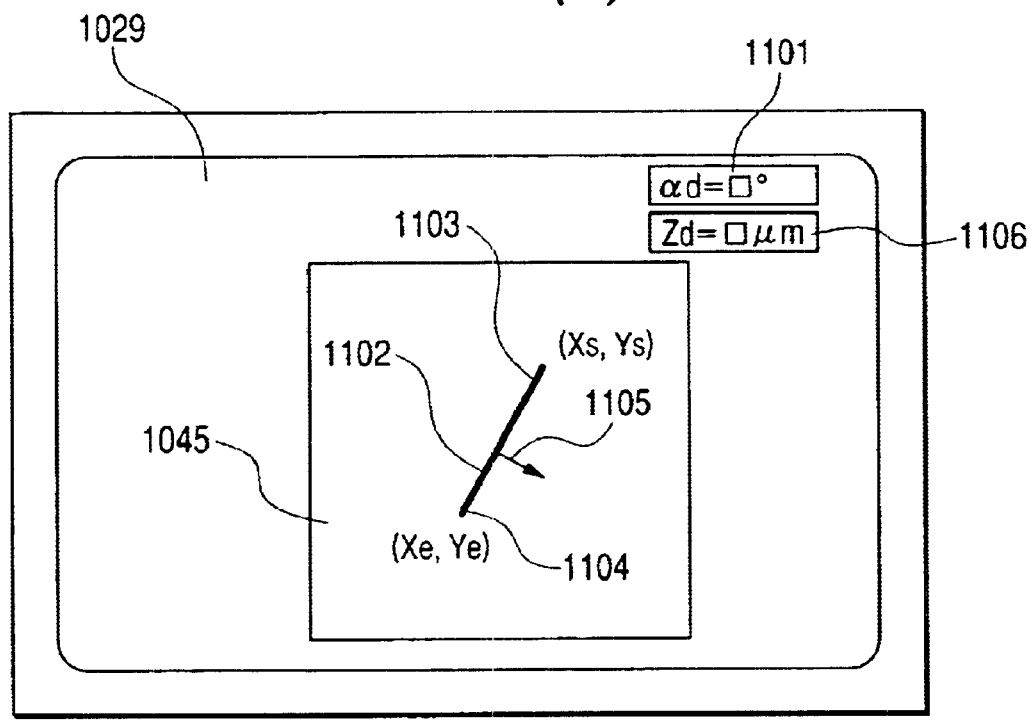
FIGS. 22(a) and 22(b) are diagrams each showing a process setting screen.

The flow of the above setting operations is expressed by a flow chart shown in FIG. 21. First, the depression angle αd of the set section is input by the user (1091). For example, as shown in FIG. 22A, by inputting the depression angle αd of the set section to a set area 1101 for set-section depression-angle on a monitor 1029, it is transmitted to a controller 1025 for ion-beam irradiating optical system via the central processing unit 1030.

Subsequently, the user sets a requested-section edge (1093). For example, as shown in FIG. 22(a), the requested-section edge is set by designating a start point (Xs, Ys) 1103 and an end point (Xe, Ye) 1104 of the requested-section edge 1102 on the secondary electron image 45. The target position can be also set from CAD (Computer-Aided Design) data of device designing. In this case, a lower layer wiring position which is not in the top surface of a sample can be also set. In the CAD data, in the step of setting the requested-section edge (1093) the start point (Xs, Ys) 1103 and the end point (Xe, Ye) 1104 of the required-section edge 1102 can be also numerically set as coordinate information. The arrow 1105 in FIG. 22(a) expresses the requested-section edge normal direction. In the direction of the arrow, an ion beam processed hole is formed.

On the basis of the above information, first, an ion beam scan range is determined. A case of tilting the ion beam scan itself for capturing a secondary electron image as described by referring to FIG. 18(b) will be described. First, the rotation angle φd for fabrication is calculated by Formula 1 (1092). By scanning an ion beam while being deflected by the rotation angle φd for fabrication, deflection coordinates (Xi, Yj) before the scanning the ion beam are converted to (Xij, Yij) expressed by Formulae 4 and 5.

$$X_{ij} = X_i \cos\phi_d + Y_j \sin\phi_d \quad \text{Formula 4}$$

$$Y_{ij} = -X_i \sin\phi_d + Y_j \cos\phi_d \quad \text{Formula 5}$$

(i=1 to n, j=1 to m) for defining the ion beam scan area are determined from the requested-section edge (Xs, Ys)

and (Xe, Ye) and a requested-section depth Zd (1095). For example, as shown in FIG. 22A, the requested-section depth Zd set in 1094 is input to a set area 1106 for the requested-section depth on the monitor 1029 and is thereby transmitted via the central processing unit 1030 to the controller 1025 for ion-beam irradiating optical system. (i=1 to n, j=1 to m) are determined from the length of the processed hole determined from the length of the requested-section edge and the width of the processed hole determined from the section observation angle and the requested-section depth Zd. Deflector voltages corresponding to (Xij, Yij) are calculated by Formulae 6 and 7 (1096).

$$V_{xij}=k_x \times X_{ij} \quad \text{Formula 6}$$

$$V_{yij}=k_y \times Y_{ij} \quad \text{Formula 7}$$

where kx and ky are coefficients of deflection in the X and Y directions, respectively, and are determined in the apparatus on the basis of the power source 1010 for acceleration voltage, the length of the deflector 1018, distance between the counter electrodes, distance between the deflector 1018 and the sample 1001, and the like. The voltage (Vxij, Vyij) is applied from the deflector power source 1017 to control the voltage of the deflector 1018. At this time, as shown by 1065 in FIG. 18(*b*), the set-section edge becomes perpendicular on the secondary electron image 1036. The specimen stage rotation angle βr necessary to make the requested-section edge 1102 coincide with the set-section edge 1065 by the turning of the specimen stage 1002 is calculated by the specimen-stage position controller 1003 by Formula 8, and the specimen stage 2 is turned.

$$\beta_r = \arctan(\cos\theta \times \tan\phi_d) - \arctan\left(\cos\theta \times \frac{X_s - X_e}{Y_s - Y_e}\right) \quad \text{Formula 8}$$

Figure 22B:
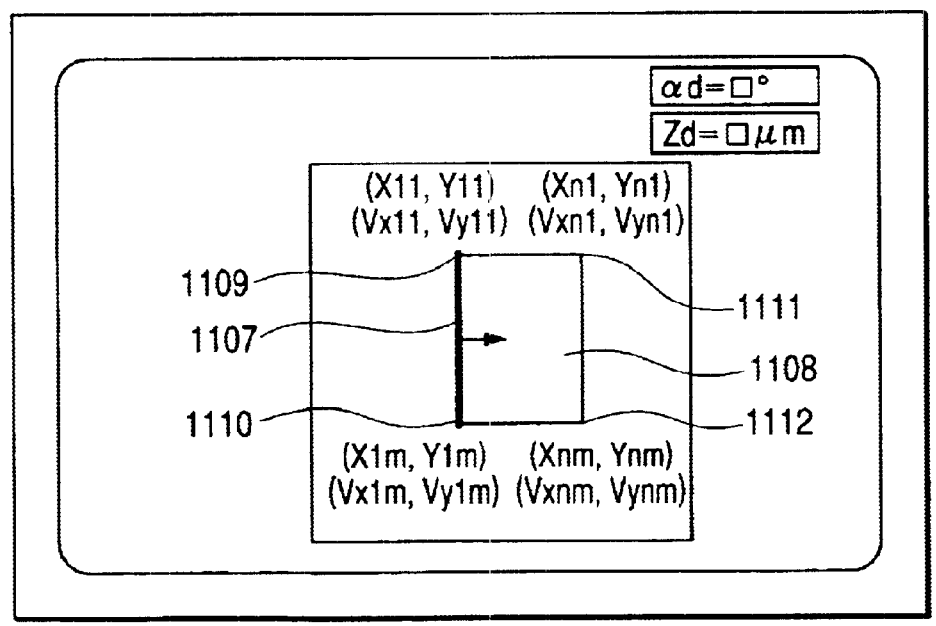

At this time, on the secondary electron image 1045, as shown in FIG. 22(*b*), an ion-beam scanning area 1108 is set as an area surrounded by (X11, Y11) 1109, (X1*m*, Y1*m*) 1110, (Xn1, Yn1) 1111, and (Xnm, Ynm) 1112 with respect to a requested-section edge 1107. By scanning the area with an ion beam so as to be processed, a requested section is formed.

If there is a process error due to flare of the ion beam and it is a problem, the deflection scan area end formed by a line segment connecting the (X11, Y11) 1109 and (X1*m*, Y1*m*) 1110 is moved to the right direction only by an amount of the error from the requested section 1107 in FIG. 22(*b*) and is set. In such a manner, the formed section becomes the requested section 1107.

An actual process example in the case where the ion beam optical axis tilt angle θ is 45° will now be described. Table 1 shows set values (in degrees, calculated to one digit to the right of the decimal) of the process rotation angle φd and the rotation angle βd of the set-section edge with respect to the depression angle αd of the set section ranging from −45° to +45° by calculating Formulae 1 and 2.

TABLE 1

| Set-section depression angle αd (degree) | Process rotation angle φd (degree) | Rotation angle of the set-section edge βd (degree) |
| --- | --- | --- |
| −45 | −90 | −90 |
| −40 | −65.4 | −57.0 |
| −30 | −45 | −35.3 |
| −20 | −28.9 | −21.3 |
| −10 | −14.2 | −10.2 |
| 0 | 0 | 0 |
| 10 | 14.2 | 10.2 |
| 20 | 28.9 | 21.3 |
| 30 | 45 | 35.3 |
| 40 | 65.4 | 57.0 |
| 45 | 90 | 90 |

Figure 26:
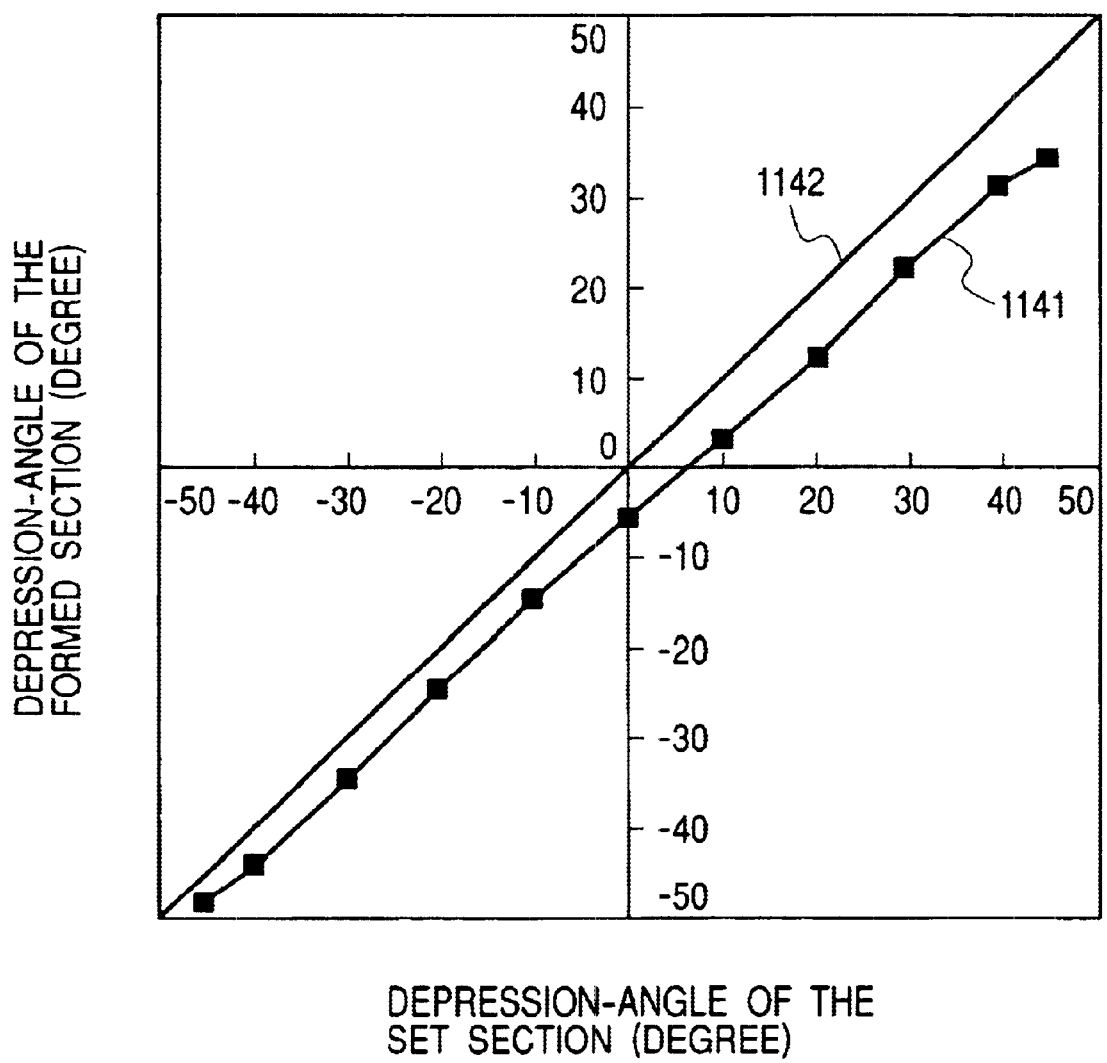
FIG. 26 is a diagram showing the relation between a depression angle of a set section and a depression angle of a formed section by experiments.

FIG. 26 shows the relation between the depression angle of the actually formed section and the depression angle αd of the set section when the process is performed under those conditions. If the process is ideally performed, an experimental value 1141 is supposed to coincide with an ideal line 1142, but they do not coincide with each other in reality. The deviation is caused by a taper formed in the process. In order to form an accurate requested section, therefore, the following flow for automatically correcting the taper angle αt is necessary.

The taper angle αt depends on not only ion beam energy, a sample material, and the like, but also the optical axis tilt angle θ of the ion beam and the requested-section depression angle αe. Consequently, when the taper angle is expressed as αt (αe, θ), by using the set-section depression angle αd expressed by the following Formula 9 to deflect φd of Formula 1 and controlling βr in Formula 8 by turning the specimen stage, the formed section and the requested section can be made coincide with each other.

$$\alpha_d = \alpha_e + \alpha_t(\alpha_e, \theta) \quad \text{Formula 9}$$

That is, by employing a table using αe and θ in the taper angle αt (αe, θ) as parameters, the section can be automatically formed in the requested section position. When θ is 45°, the table is as shown in Table 2.

TABLE 2

| Requested-section depression angle αe (degree) | Taper angle αt (degree) |
| --- | --- |
| −45 | 3.4 |
| −40 | 3.8 |
| −30 | 4.6 |
| −20 | 5.4 |
| −10 | 6.2 |
| 0 | 7.0 |
| 10 | 7.7 |
| 20 | 8.5 |
| 30 | 9.3 |
| 40 | 10.1 |
| 45 | 10.5 |

As described above, with the configuration of the invention, by automatically controlling the rotation angle φd of process setting and the rotation angle βr of the specimen stage, the tilt irradiation angle αd of an ion beam can be arbitrarily selected, and taper eliminating process or the like is also facilitated.

Seventh Embodiment

In a seventh embodiment, an example where a shape to be actually processed for forming a section is a rectangle will be described.

Figure 27A:
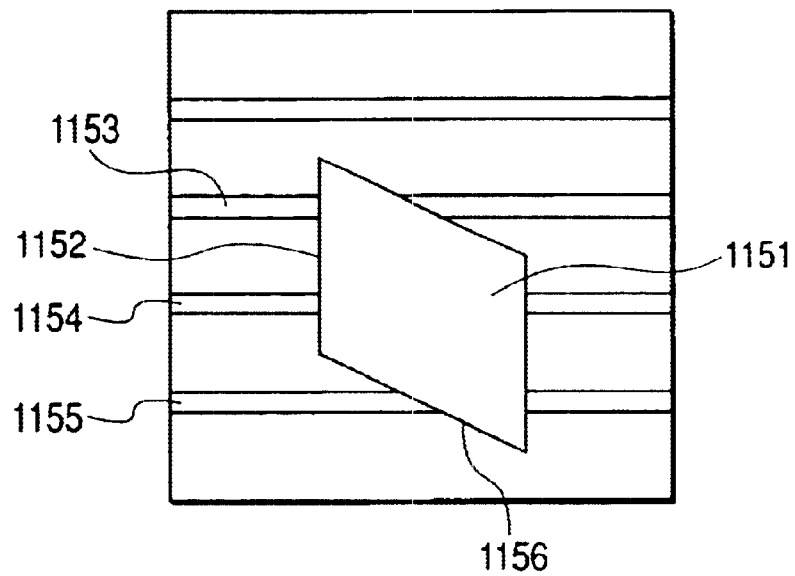
FIGS. 27(a) and 27(b) are diagrams showing a difference between device pattern processes according to sample surface process shapes.

Since the ion beam scanning area described in the sixth embodiment has a rectangular shape as shown in FIG. 18(a), the shaped actually processed on the sample surface is a parallelogram as shown by 1151 in FIG. 27(a). Reference numerals 1153, 1154, and 1155 are metal lines of a device and an object is to process the positions of the metal lines 1153 and 1154. A formed-section edge 1152 is processed so as to cross perpendicular to the metal lines 1153 and 1154. In this case, a processed edge 1156 other than the formed section edges is formed obliquely with respect to the formed-section edge 1152 and there is a case such that the metal line 1155 which is inherently unnecessary to be processed is also processed.

Figure 27B:
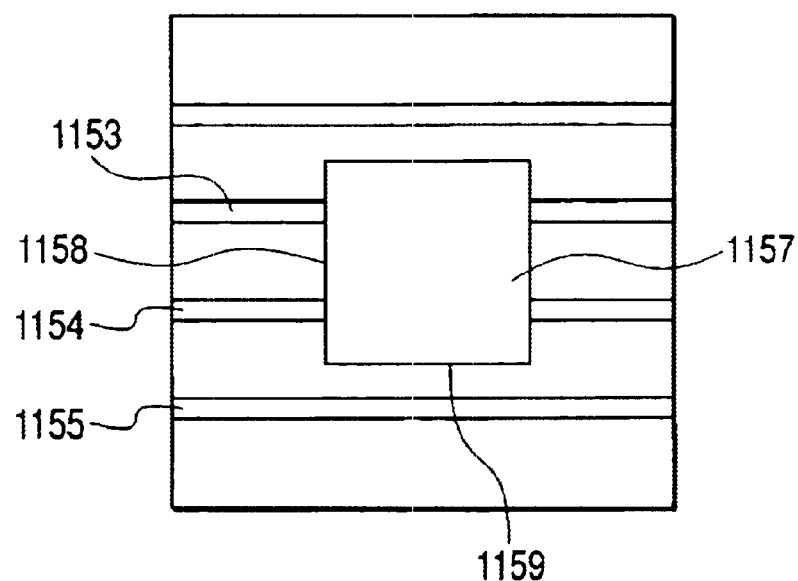

Consequently, in some cases, a process as shown in FIG. 27(b) is desired. Specifically, the processed shape on the sample surface is set to a rectangle as shown by 1157, and a processed edge 1159 other than a formed-section edge 1158 is made parallel to the metal line 1153 and the like, thereby enabling only the target metal lines 1153 and 1154 to be processed.

Figure 28:
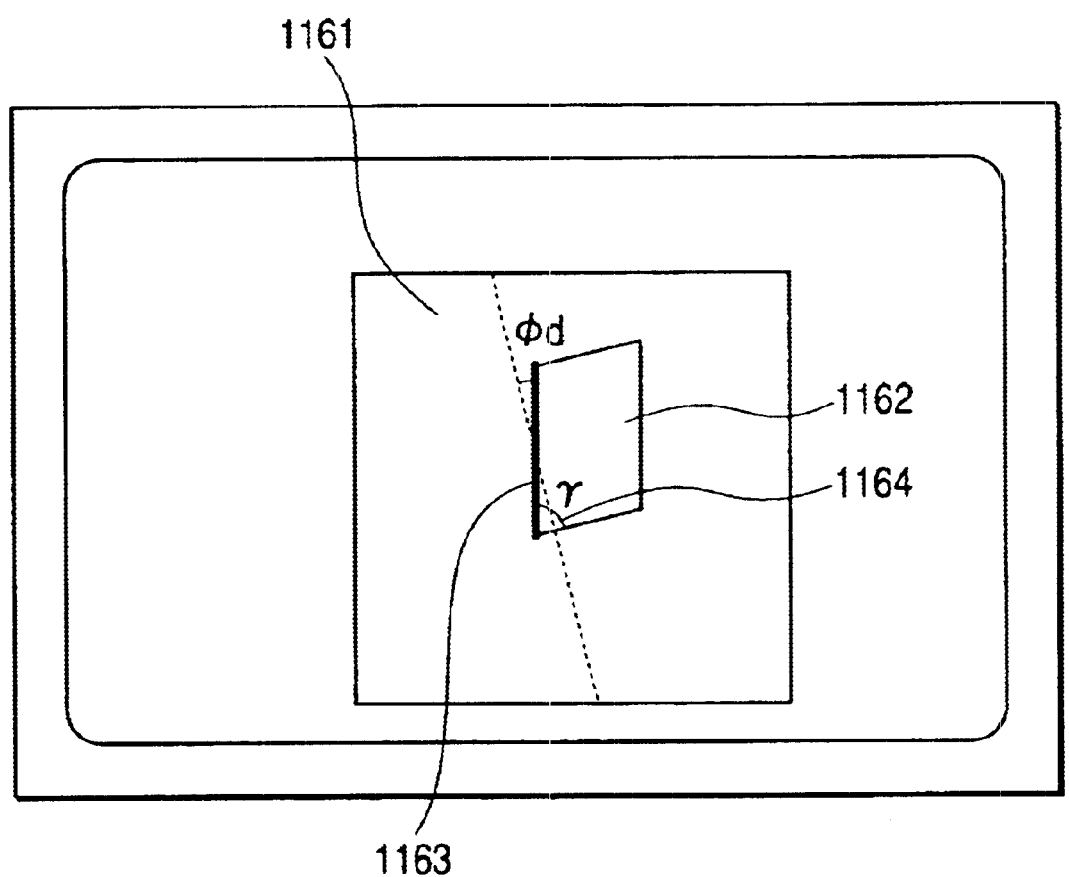
FIG. 28 is a diagram showing a scanning area for forming a rectangular hole.

In order to realize the process, it is sufficient to make process setting shown in FIG. 28. FIG. 28 corresponds to FIG. 18(b) and shows that the whole secondary electron image 1161 is turned by $\phi d$. In this case, although a scanning-area edge 1163 is set in a manner similar to the set-section edge 1065 in FIG. 18(b), a scanning area 1162 is set in a parallelogram different from the rectangular-shaped scanning area 1066. An interior angle $\gamma$ (shown in degrees) of the parallelogram indicated by 1164 is expressed by Formula 10.

$$\gamma = 90 - \phi_d + \arctan\{(\cos\theta)^2 \times \tan\phi_d\} \qquad \text{Formula 10}$$

As described above, by performing a process by setting the scanning area 1162 in the parallelogram shape, the rectangular process of FIG. 27(b) can be realized, so that an arbitrary tilt process can be realized without processing an unnecessary area.

Eighth Embodiment

In an eighth embodiment, an example of applying the sample fabricating apparatus according to the invention to a membrane sample for TEM observation, energy dispersive X-ray spectrometry (EDX), or electron energy loss spectroscopy (EELS) will be described.

Figure 23:
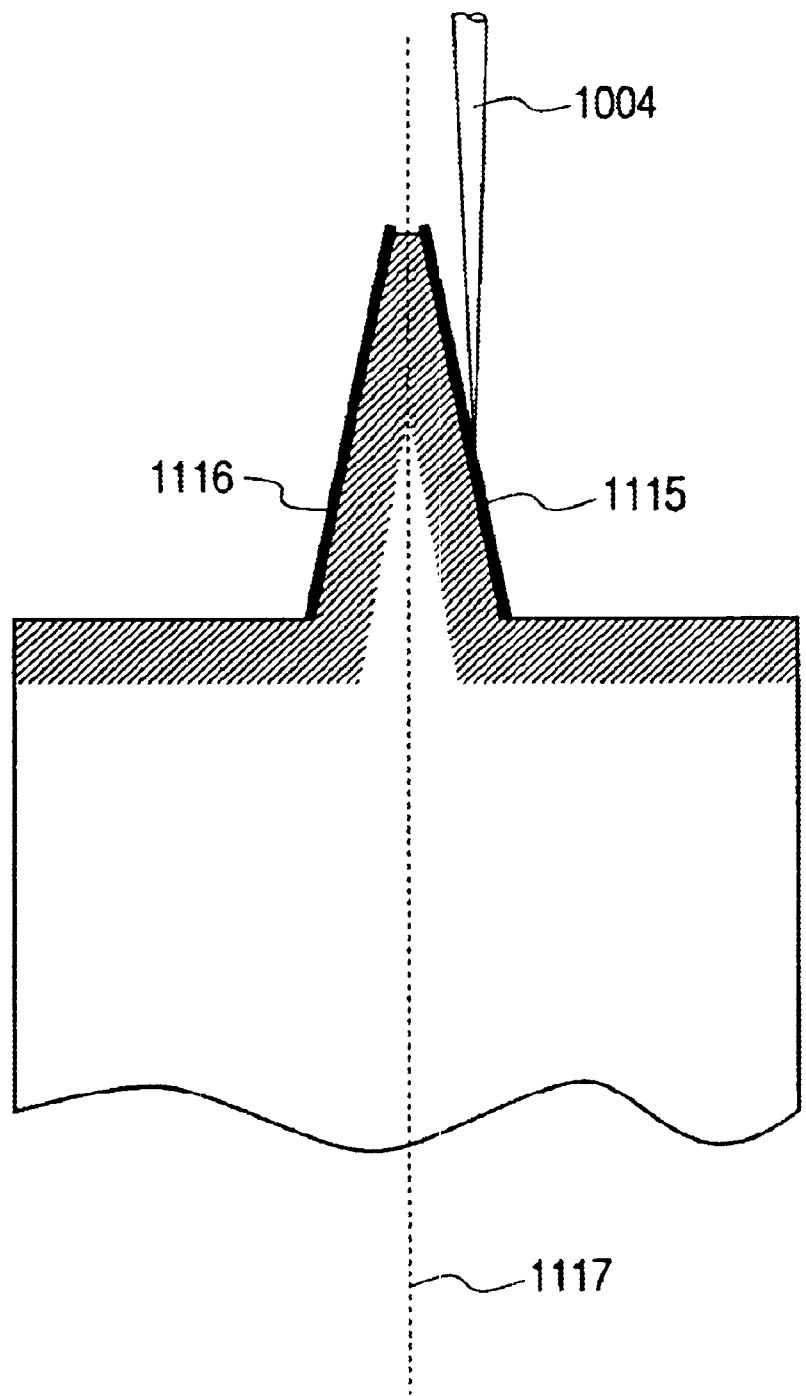
FIG. 23 is a diagram showing a membrane forming process by parallel irradiation of an ion beam for a requested section.

The membrane for TEM observation is requested to be thin in order to improve observation resolution and is usually processed to a thickness of about 100 nm. However, in the case of irradiating an observation section with an ion beam in parallel as described in the sixth embodiment, when the TEM membrane is processed, tapered membrane sections 1115 and 1116 as shown in FIG. 23 are formed. Consequently, a sample has a thickness distribution in the depth direction with respect to a requested observation section 1117. In this case, an extra structure is also included in a deep area, so that the observation accuracy deteriorates. Further, in the case of using the EDX or EELS for analyzing a composition element, quantitativeness of the signal amount of an X-ray and an electron beam is important. In the case of a sample of which film thickness varies as shown in FIG. 23, the quantitative analysis of compositions cannot be carried out.

Figure 24A:
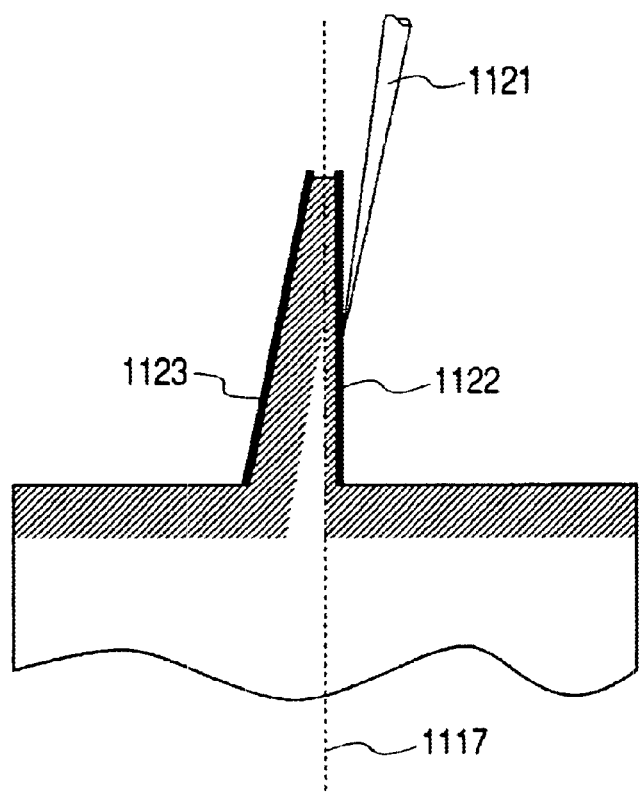
FIGS. 24(a) and 24(b) are diagrams each showing a membrane forming process with a tilted ion beam for a requested section.
Figure 24B:
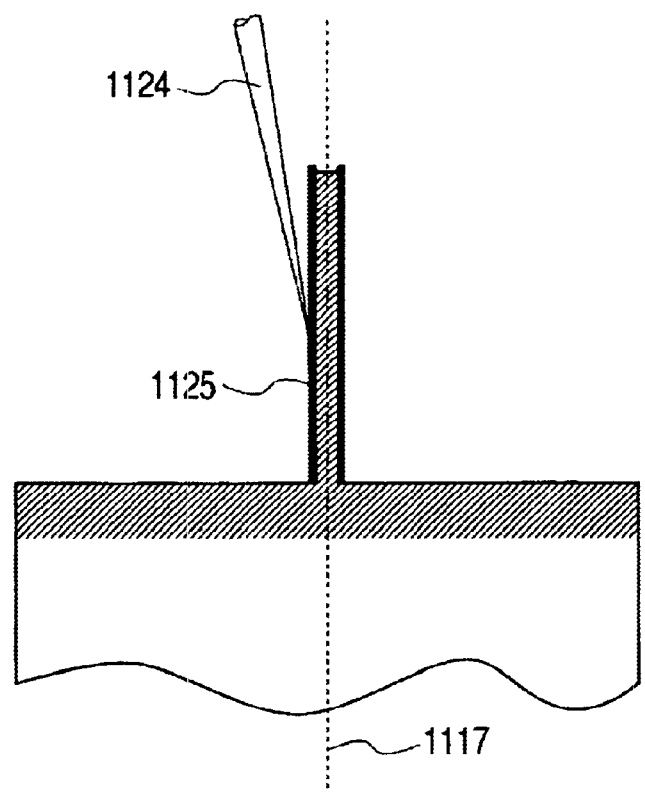

In order to solve the problem, as described in the sixth embodiment, the rotation angle $\phi d$ of processing setting of an ion beam is controlled by the controller 1025 for ion-beam irradiating optical system, and the requested observation section 1117 is obliquely irradiated with an ion beam 1121, thereby enabling a membrane section 1122 to be formed in parallel with the requested observation section 1117, as shown in FIG. 24(a). Similarly, by setting the rotation angle $\phi d$ of process setting of the ion beam in the opposite direction, a tilted ion beam 1124 shown in FIG. 24(b) can be emitted, so that a membrane section 1125 can be formed. Thus, an observation membrane having high uniformity in film thickness can be formed.

As described above, with the configuration of the embodiment, by automatically controlling the rotation angle $\phi d$ of process setting and the rotation angle $\beta r$ of the specimen stage, the tilt irradiation angle $\alpha d$ of an ion beam can be arbitrarily selected, and a membrane having high thickness uniformity can be formed. Thus, the embodiment is effective at improving the observation accuracy of the TEM observation and making quantitative analysis of EDX or EELS.

Ninth Embodiment

In a ninth embodiment, an example of applying the sample fabricating apparatus according to the invention to a sample for analyzing the composition in the depth direction of Auger electron spectroscopy (AES) or secondary ion mass spectroscopy (SIMS) will be described.

Figure 25A:
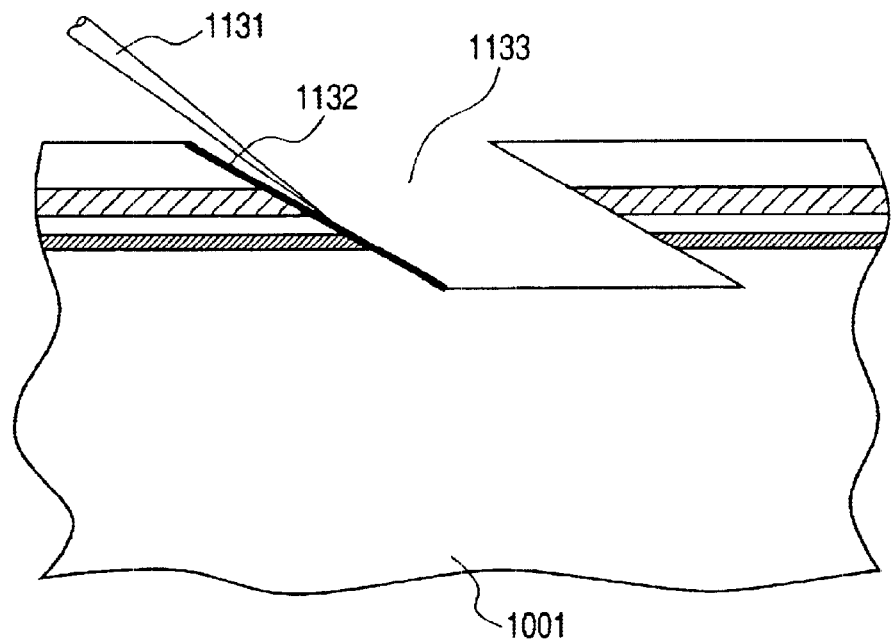
FIGS. 25(a) and 25(b) are diagrams each showing a process for forming a sample section adapted to analyze composition in the depth direction.
Figure 25B:
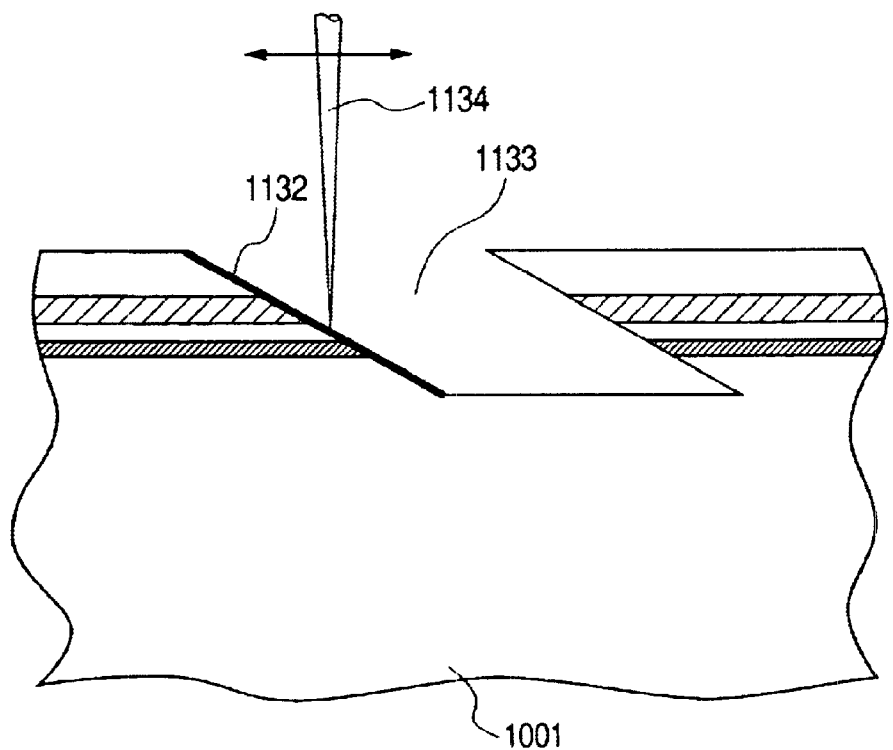

In the case of analyzing a composition in the depth direction of a sample portion in which the composition is uniform in the direction parallel to the surface of the sample by AES or SIMS, by analyzing a section formed at a small angle to improve the resolution in the depth direction, the depth resolution can be improved. FIGS. 25(a) and 25(b) show a method of preparing a section suitable for such analysis.

An ion beam 1131 is emitted while being deflected by the ion beam deflecting control described in the sixth embodiment to form a hole 1133. By forming a section 1132 in such a manner, the sample internal structure exposed in the section is wider than that in the sample depth direction. The formed section 1132 is irradiated with an electron beam 1134, Auger electrons are detected and dispersed, and an in-plane composition distribution in the formed section 1132 is obtained, thereby obtaining a composition distribution in the depth direction of the sample 1001. The method can be also used for element analysis in the depth direction by the SIMS by emitting an ion beam in place of the electron beam 1134, detecting secondary ions, and performing mass spectrometry.

As described above, by forming the tapered section at a small angle by the sample fabricating apparatus, the resolution of analysis of composition in the depth direction of AES, SIMS, or the like can be also improved.

Although the embodiment has been described by using the process with an ion beam as an example, the invention can be applied to a process using, not necessarily the ion beam, but a charged particle beam which can be processed.

In the sample fabricating method according to the invention, in the series of processes for separating a micro sample from a specimen stage, the angle formed between the FIB and the sample surface is not changed, so that the process for tilting the stage is not included. In the sample fabricating method of the invention, therefore, even when the function of tilting the specimen stage is omitted to reduce the size of the whole apparatus, preparation of a sample for analyzing, observing, or measuring a micro area by sepa rating a micro sample from a sample or preparing the micro sample to be separated can be realized. Also in the case of the apparatus in which the specimen stage has the tilting function, time required to tilt the stage is unnecessary, so that sample fabrication time is made relatively short. The problem such that the sample surface cannot be observed before and after the specimen stage is tilted can be also reduced.

According to the invention, the sample fabricating apparatus for preparing a sample for analyzing, observing, or measuring a micro area by separating a micro sample from a sample or preparing the micro sample to be separated, which is suitable from the viewpoint that the operation of the apparatus can be automated and the burden on the operator can be lessened is provided.

According to the invention, with the configuration of the apparatus using the not-tilted specimen stage effective at reducing the apparatus manufacturing cost, an ion beam can be emitted at an arbitrary angle and a very accurate section can be formed, so that the precision of FIB or SEM observation can be increased. A sample membrane having uniform film thickness can be formed, so that it is effective at improving the precision of the TEM observation and making quantitative analysis of EDX and EELS.

What is claimed is:

1. A sample fabricating method comprising:
    a step of placing a sample on a specimen stage;
    a first processing step of processing the sample by irradiating the sample with an ion beam deflected relative to a sample placement face of said specimen stage;
    a second processing step of processing the sample by turning the sample on the sample placement face and irradiating the sample with an ion beam; and
    a step of extracting a sample piece obtained in said second processing step.

2. A sample fabricating apparatus, comprising: at least a focused ion beam irradiating optical system, a secondary particle detector for detecting secondary particles generated from a sample irradiated with a focused ion beam, and a specimen stage on which a specimen base is placed, for separating a micro sample from said specimen base or preparing the micro sample to be separated by irradiating a peripheral area of the micro sample with the focused ion beam in a plurality of incident directions to said specimen base, wherein said focused ion beam irradiating optical system is provided with a focused ion beam tilting function of changing an optical axis of the focused ion beam emitted to the sample by at least 15 degrees, wherein said focused ion beam tilting function of changing the optical axis of the focused ion beam emitted to the sample by at least 15 degrees is realized by an electric deflecting mechanism.

* * * * *